US010702399B2

(12) United States Patent
Jordan et al.

(10) Patent No.: US 10,702,399 B2
(45) Date of Patent: Jul. 7, 2020

(54) POSTERIOR STABILIZED INSERT TRIAL WITH ADJUSTABLE POST

(71) Applicants: Smith & Nephew, Inc., Memphis, TN (US); Theodore P. Firestone, Paradise Valley, AZ (US)

(72) Inventors: Jason S. Jordan, Hernando, MS (US); Theodore P. Firestone, Paradise Valley, AZ (US)

(73) Assignee: Smith & Nephew, Inc., Memphis, TN (US)

( * ) Notice: Subject to any disclaimer, the term of this patent is extended or adjusted under 35 U.S.C. 154(b) by 218 days.

(21) Appl. No.: 14/363,758

(22) PCT Filed: Dec. 6, 2012

(86) PCT No.: PCT/US2012/068188
§ 371 (c)(1),
(2) Date: Jun. 6, 2014

(87) PCT Pub. No.: WO2013/086150
PCT Pub. Date: Jun. 13, 2013

(65) Prior Publication Data
US 2014/0371865 A1 Dec. 18, 2014

Related U.S. Application Data

(60) Provisional application No. 61/567,975, filed on Dec. 7, 2011.

(51) Int. Cl.
*A61F 2/38* (2006.01)
*A61F 2/30* (2006.01)
*A61F 2/46* (2006.01)

(52) U.S. Cl.
CPC ............ *A61F 2/4684* (2013.01); *A61F 2/389* (2013.01); *A61F 2/3886* (2013.01);
(Continued)

(58) Field of Classification Search
CPC .......... A61F 2/389; A61F 2/38; A61F 2/4684; A61F 2/3859; A61F 2/3868; A61F 2/28;
(Continued)

(56) References Cited

U.S. PATENT DOCUMENTS 4,586,933 A    5/1986  Shoji et al.
5,019,105 A *  5/1991  Wiley ...................... A61F 2/34
                                                        623/22.29

(Continued)

OTHER PUBLICATIONS

International Search Report dated Mar. 25, 2013 for PCT/US2012/068200.
(Continued)

*Primary Examiner* — Ann Schillinger

(57) ABSTRACT

Trial joint inserts have posts at different positions relative to the base. During joint replacement surgery, a surgeon can test different positions for a post using a trial insert, identify a suitable position for the post, and then select a permanent insert with a post in the desired position. The devices and methods in this application allow a surgeon to provide an individualized joint replacement for a patient. Joint inserts may be configured so the post moves relative to the base. The post may be adjustably positionable, may lock in place, or may be actuated by a resistance member such as a spring.

20 Claims, 17 Drawing Sheets

(52) U.S. Cl.
CPC . *A61F 2002/305* (2013.01); *A61F 2002/3039* (2013.01); *A61F 2002/30387* (2013.01); *A61F 2002/30553* (2013.01); *A61F 2002/30617* (2013.01)

(58) Field of Classification Search
CPC .. A61F 2/30734; A61F 2/30; A61F 2002/305; A61F 2002/30599; A61F 2002/30604; A61F 2002/3082; A61F 2002/30892; A61F 2/3886; A61F 2002/30617
See application file for complete search history.

(56) References Cited

U.S. PATENT DOCUMENTS

| | | | |
|---|---|---|---|
| 5,733,292 A | 3/1998 | Gustilo et al. | |
| 5,782,925 A | 7/1998 | Collazo et al. | |
| 5,906,643 A | 5/1999 | Walker | |
| 6,004,352 A * | 12/1999 | Buni | A61F 2/3886 623/20.33 |
| 6,306,172 B1 | 10/2001 | O'Neil et al. | |
| 6,500,208 B1 * | 12/2002 | Metzger | A61F 2/389 623/20.15 |
| 6,660,039 B1 | 12/2003 | Evans et al. | |
| 6,926,738 B2 * | 8/2005 | Wyss | A61F 2/3886 623/18.11 |
| 6,986,791 B1 * | 1/2006 | Metzger | A61F 2/3868 623/20.24 |
| 7,175,666 B2 | 2/2007 | Yao | |
| 7,255,715 B2 | 8/2007 | Metzger | |
| 7,297,164 B2 | 11/2007 | Johnson et al. | |
| 7,547,327 B2 | 6/2009 | Collazo | |
| 2003/0153979 A1 | 8/2003 | Hughes et al. | |
| 2005/0113932 A1 | 5/2005 | Kovacevic | |
| 2006/0030945 A1 * | 2/2006 | Wright | A61F 2/30721 623/20.15 |
| 2006/0111790 A1 | 5/2006 | Dietz | |
| 2011/0066247 A1 | 3/2011 | Ries et al. | |
| 2014/0364956 A1 * | 12/2014 | Jordan | A61F 2/3886 623/20.33 |

OTHER PUBLICATIONS

International Search Report for PCT/US2012/068188 dated Mar. 25, 2013.

* cited by examiner

POSTERIOR STABILIZED INSERT TRIAL WITH ADJUSTABLE POST

CROSS-REFERENCE TO RELATED APPLICATIONS

This application is a United States National Stage filing under 35 U.S.C. § 371 of International Application No. PCT/US2012/068188, filed on Dec. 6, 2012, which claims the benefit of U.S. Provisional Application No. 61/567,975, filed Dec. 7, 2011, each of which is hereby incorporated by reference herein in its entirety. International Application No. PCT/US2012/068188 was published under PCT Article 21(2) in English.

BACKGROUND

Total knee replacement is a common reconstructive procedure. Advances in technique, instrumentation and design over the last 20 years have allowed for improved results with regards to pain relief, return to function and overall quality of life. Over 500,000 patients have knee replacement surgery each year. Total knee arthroplasty surgery typically involves affixing a femoral component to the end of a patient's femur, affixing a tibial component to the top of a patient's tibia, and inserting a tibial insert to serve as a spacer between the two components. The tibial insert has a base that is fixed to the tibial component and, in posterior cruciate substituting designs, a posterior stabilizing post that contacts the femoral component. The femoral component rolls and slides on the tibial insert while the knee flexes until the post contacts a cam on the femoral component. This contact point determines the amount of rollback of the femoral component relative to the tibial component. The human knee and many knee replacements display rollback at high flexion. Rollback is when the femur's contact point with the tibia moves towards the posterior of the tibia. This rollback movement is extremely variable in cruciate retaining designs and in vivo fluoroscopic studies have actually demonstrated paradoxical anterior translation of the femur on the tibia with flexion. One of the advantages of posterior stabilized design is a more predictable pattern of femoral rollback as the knee flexes.

A replacement joint may be customized relative to the patient's anatomy. Preferred replacement joints allow the patient an optimal degree of rollback. Some rollback is often desirable to mimic the behavior of the natural knee, but excessive rollback may be detrimental because it overstretches the soft tissues surrounding the joint (e.g., the patellar tendon and quadriceps). Over-stretching of these tissues can cause the tissues to tighten, ultimately restricting the patient's movement. Because soft joint tissue structures vary from patient to patient, no single joint replacement may be appropriate for all patients.

In the past, surgeons have tested different trial tibial inserts during total knee arthroplasty surgery in order to identify an appropriate permanent tibial insert. Different thicknesses of trial tibial inserts have been tested in order to identify a suitable insert for a patient. However, currently, the placement of the insert's posterior stabilizing post relative to its base is not selectable at the time of surgery. There is a distinct need for an implant with a variable positioned post. There is also a need for a trial insert with a customizable posterior stabilizing post that a surgeon can evaluate intraoperatively.

SUMMARY

This application describes systems, devices, and methods related to trial joint inserts with posts at different positions. Testing trial inserts with differently positioned posterior stabilizing posts allows a user to select a permanent insert with a post at a desired position, tailored to the patient. In total knee arthroplasty surgery, a surgeon can control the maximum rollback of the replacement joint by selecting a joint replacement insert with a posterior stabilizing post (or simply "post") in a particular position along the anterior/posterior axis of the insert's base. A post close to the posterior end of the insert may allow more rollback than a post close to the anterior end of the insert. Because soft joint tissue structures vary from patient to patient, selecting the post location helps provide a better patient fit. In addition, the ability of a patellar component to "track" in the trochlear groove of the femoral component is largely determined by femoral rollback. One reason surgeons often need to perform a lateral patella release at the time of surgery is excessive rollback resulting in excessive tension on the extensor mechanism. Thus, by selecting a post position that avoids excessive rollback, a surgeon can reduce the likelihood that lateral patella release surgery will be required. Selecting an appropriate post position also allows a surgeon to influence the tibial slope in order to, e.g., promote knee function and reduce wear.

In certain embodiments, the present disclosure provides an orthopedic insert comprising: a base and a posterior stabilizing post coupled to the base, the post is adjustably positionable relative to the base. In certain embodiments, the orthopedic implant is a tibial insert. In certain embodiments, the orthopedic implant is a hinge (ginglymus) joint. In certain embodiments, the hinge joint is selected from the group consisting of: a knee joint, an elbow joint, an ankle joint, an interphalangeal articulation of the hand, or an interphalangeal articulation of the foot. In certain embodiments, the insert further comprises a locking insert that locks the post in place relative to the base. In certain embodiments, the base has a trough and the posterior stabilizing post is disposed within the trough and slides within the trough. The insert may further comprise a post marking on the post and a plurality of base markings on the base. In some aspects, the post locks in place at intervals corresponding to the base markings. In certain aspects, the locking insert is selected from a ball and detent, screws, or tabs. In some aspects, the insert is a non load-bearing trial insert. In other aspects, the insert is a load-bearing insert.

This application also provides a knee implant comprising: a tibial component shaped to align with and support the proximal end of a patient's tibia, a femoral component shaped to align with and support the patient's femur; and a tibial insert as described herein.

In addition, this disclosure provides a method of selecting a load-bearing tibial insert, comprising: placing a trial tibial insert in a patient, the trial comprising: a base and a sliding posterior stabilizing post; evaluating at least two fits of the trial insert relative to fitting criteria, in which the first fit includes the post being located at a first position relative to the base and the second fit includes the post being located at a second position relative to the base; determining a desired location of the post based on the evaluation of the fits; and selecting a load-bearing tibial insert comprising: a base connected to a posterior stabilizing post at a position corresponding to the determined location. In certain aspects, the evaluation of the fits comprises evaluations of a degree of anterior soft tissue stretching relative to a standard. In some aspects, selecting the permanent tibial insert comprises: selecting a permanent tibial insert with a posterior stabilizing post coupled to a base, sliding the post to the determined position relative to the base, and locking the post in place at the determined position.

This disclosure also provides a method of selecting a load-bearing tibial insert, comprising: placing a trial tibial insert in a patient, the trial insert comprising a base and a posterior stabilizing post, which post is adjustably positionable relative to the base; evaluating at least two fits of the trial insert relative to fitting criteria, in which the first fit includes the post being located at a first position relative to the base and the second fit includes the post being located at a second position relative to the base; determining a desired location of the post based on the evaluation of the fits; and selecting a load-bearing tibial insert comprising a base connected to a posterior stabilizing post at a position corresponding to the determined location. In certain embodiments, the evaluation of the fits comprises evaluations of a degree of anterior soft tissue stretching relative to a standard. In certain embodiments, the selecting the load-bearing tibial insert comprises: selecting a load-bearing tibial insert comprising a base with a posterior stabilizing post coupled to the base, and a locking insert and positioning the post to the determined location relative to the base and locking the post in place at the determined location.

This disclosure also provides a tibial insert comprising: a base, a posterior stabilizing post coupled to the base in which the post is configured to slide relative to the base, and a resistance member disposed within the base, the resistance member compressing or extending when the posterior stabilizing post slides with respect to the base. In certain embodiments, the resistance member is affixed to the base. In certain embodiments, the insert is configured to attach immovably to a tibial component. In some aspects, the resistance member is disposed in a trough in the base, the trough having anterior and posterior interior ends, with a first end of the resistance member contacting an interior end of the trough and a second end of the resistance member contacting the post. The first end of the resistance member may contact the anterior interior end of the trough. In certain embodiments, the resistance member may be a spring.

In addition, this disclosure provides a tibial insert comprising: a base; a posterior stabilizing post coupled to the base and configured to slide relative to the base; and a resistance member disposed within the base, the resistance member compressing or extending when the posterior stabilizing post slides with respect to the base. In certain embodiments, the resistance member is affixed to the base. In certain embodiments, the insert is configured to attach immovably to a tibial component. In certain embodiments, the resistance member is disposed in a trough in the base, the trough having anterior and posterior interior ends, with the first end of the resistance member contacting an interior end of the trough and a second end of the resistance member contacting the post. In some embodiments, the first end of the resistance member contacts the anterior interior end of the trough. In certain embodiments, the resistance member is a spring.

In addition, this disclosure provides a tibial insert comprising: a base; a spring-actuated posterior stabilizing post coupled to the base and configured to slide relative to the base; in which the spring compresses or extends when the posterior stabilizing post slides with respect to the base.

In addition, this disclosure provides a method of selecting a load-bearing tibial insert, comprising: sequentially placing at least two trial inserts in a patient, each trial insert comprising a base immovably connected to a posterior stabilizing post, the post being disposed at a different location on the base in each trial insert; evaluating a fit of each trial insert relative to fitting criteria; determining a desired location of the post based on the evaluation of the fit, and selecting a permanent tibial insert comprising a base immovably connected to a posterior stabilizing post at a position corresponding to the determined location.

In addition, this disclosure provides a kit comprising at least two tibial inserts, each insert comprising: a base; and a posterior stabilizing post immovably coupled to the base, the post being disposed at a different location on the base in each insert. In certain embodiments, the base has an anterior-posterior axis, with the post of the first trial insert being immovably coupled to the base at a neutral position along the anterior-posterior axis, and the post of the second trial insert being immovably coupled to the base in a position which is anterior of or posterior to the neutral position. In certain embodiments, the tibial insert is a non load-bearing tibial insert. In alternative embodiments, the tibial insert is a load-bearing tibial insert.

Further areas of applicability of the disclosed methods, systems, and devices will become apparent from the detailed description provided hereinafter. It should be understood that the detailed description and specific examples, while indicating particular embodiments, are intended for purposes of illustration only and are not intended to limit the scope of the disclosure or any claims that may be pursued.

BRIEF DESCRIPTION OF THE DRAWINGS

The foregoing and other objects and advantages will be appreciated more fully from the following further description thereof, with reference to the accompanying drawings. These depicted embodiments are to be understood as illustrative and not as limiting in any way.

DETAILED DESCRIPTION

To provide an understanding of the systems, devices, and methods described herein, certain illustrative embodiments will now be described. For the purpose of clarity and illustration, the systems, devices, and methods are described primarily with respect to orthopedic knee implants. It will be understood by one of ordinary skill in the art that the systems, devices, and methods described herein may be adapted and modified as is appropriate, and that the systems, devices and methods described herein may be employed in other suitable applications, such as for other types of joints and orthopedic implants. The systems, devices, and methods are particularly appropriate for other hinge joints such as the elbow and knuckle. Such other additions and modifications will not depart from the scope hereof.

Figure 1A:
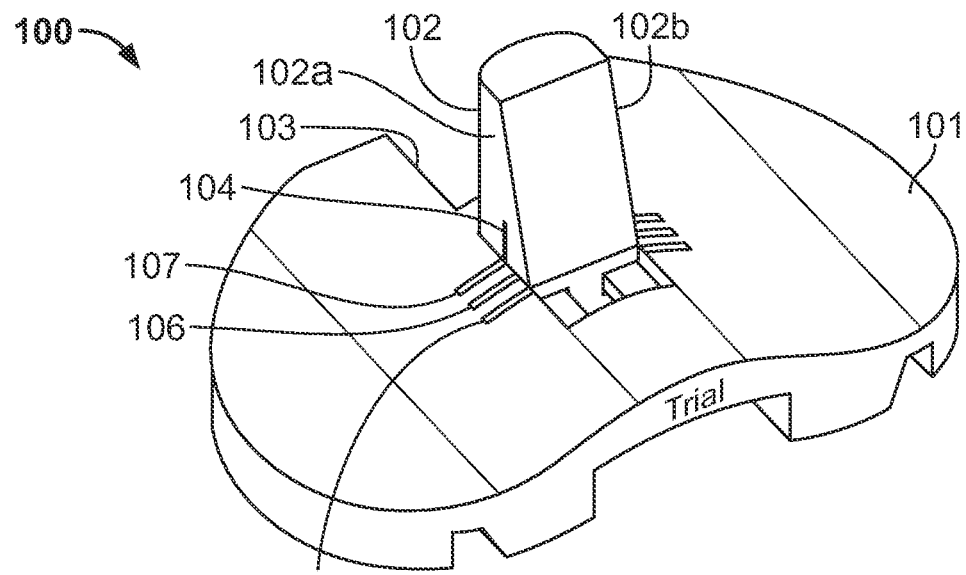
FIGS. 1A-C are perspective views of a trial tibial insert with an adjustably positionable posterior stabilizing post. Panels A-C show the posterior stabilizing post in different positions along the anterior/posterior axis.
Figure 1B:
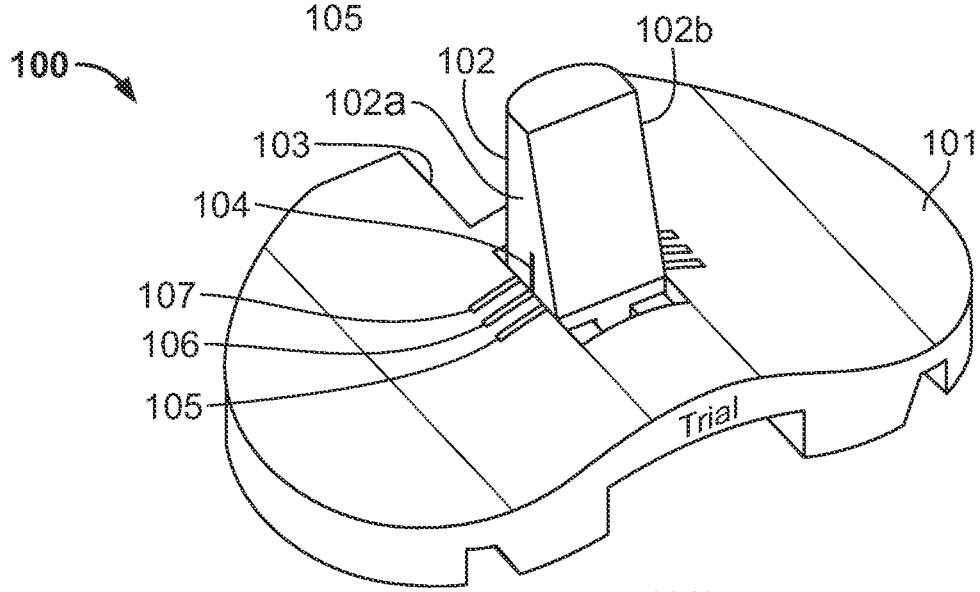
Figure 1C:
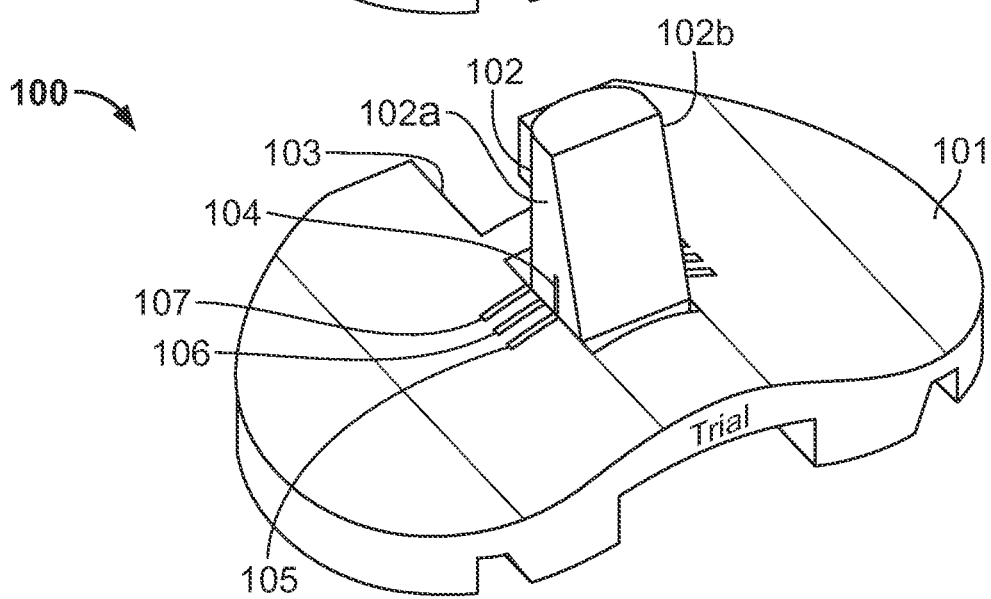

FIGS. 1A-C show a tibial trial insert 100. The insert comprises an adjustably positionable posterior stabilizing post 102 capable of locking in place at different positions relative to a base 101. Panels A-C show the posterior stabilizing post in different positions.

The posterior stabilizing post 102 is disposed at an angle with the base 101. The posterior stabilizing post is designed to couple to a femoral component. This post 102 stabilizes the entire replacement joint, performing a function analogous to the posterior cruciate ligament (PCL). In some embodiments the post 102 and the femoral component are in direct contact. The anterior face of the posterior stabilizing post is slanted and the posterior face is substantially perpendicular to the base. The posterior stabilizing post slides along the base 101 and locks in place at desired locations relative to the base. FIG. 1A shows the posterior stabilizing post in the neutral position, FIG. 1B shows the posterior stabilizing post in the anterior +2 position, and FIG. 1C shows the posterior stabilizing post in the anterior +4 position. The posterior stabilizing post optionally comprises a post marking 104 that helps a user determine the position of the post at a glance. The post 102 has markings on both the lateral side 102a and medial side 102b, or may have a marking on just one of the sides. The post marking 104 can be any visual marking, for instance, a raised ridge, a channel, or a biocompatible paint or dye.

The base 101 supports the posterior stabilizing post 102. The base is configured to be coupled to a tibial component so that the insert 100 lies between the tibial component and the femoral component in a knee replacement setting. In some embodiments the base and tibial component are in direct contact. The base may be ovoid and have the same radii as the tibial component to which it attaches. The base includes a cruciate notch 103 through which the patient's anterior cruciate ligament (ACL) passes. Typically, the anterior portion of the base is slightly raised in order to match the curve of the anterior portion of the femoral component. The base optionally comprises base markings 105, 106, and 107. The base markings can be any visual marking, for instance, a raised ridge, a channel, or a biocompatible paint or dye, or any other suitable marking, or any combination thereof. In FIGS. 1A-1C, there are three base markings spaced at 2 mm intervals. However, the base markings can be more or less numerous (e.g., 2, 3, 4, 5, or more) and the spacing of the markings (e.g., 1 mm, 2 mm, or 3 mm) can also be adjusted. When a user moves the posterior stabilizing post from one position to another, the post marking 104 lines up with one of the base markings (or falls between two markings) so that the user can determine the position of the post at a glance. An adjustably positionable posterior stabilizing post similar to that in FIG. 1 can also be used in a permanent tibial insert.

Figure 2A:
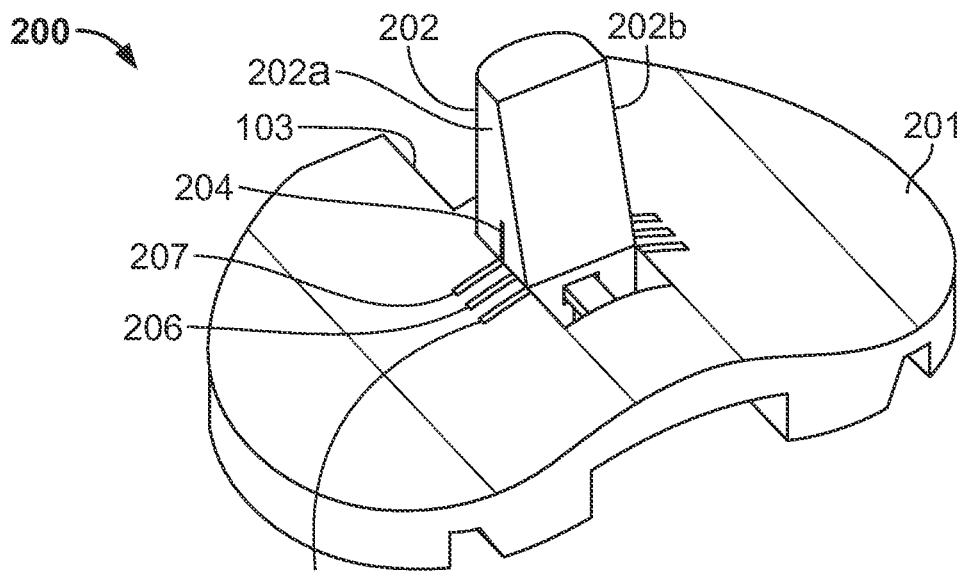
FIGS. 2A-C are perspective views of a permanent tibial insert with an adjustably positionable posterior stabilizing post. Panels A-C show the posterior stabilizing post in different positions along the anterior/posterior axis.
Figure 2B:
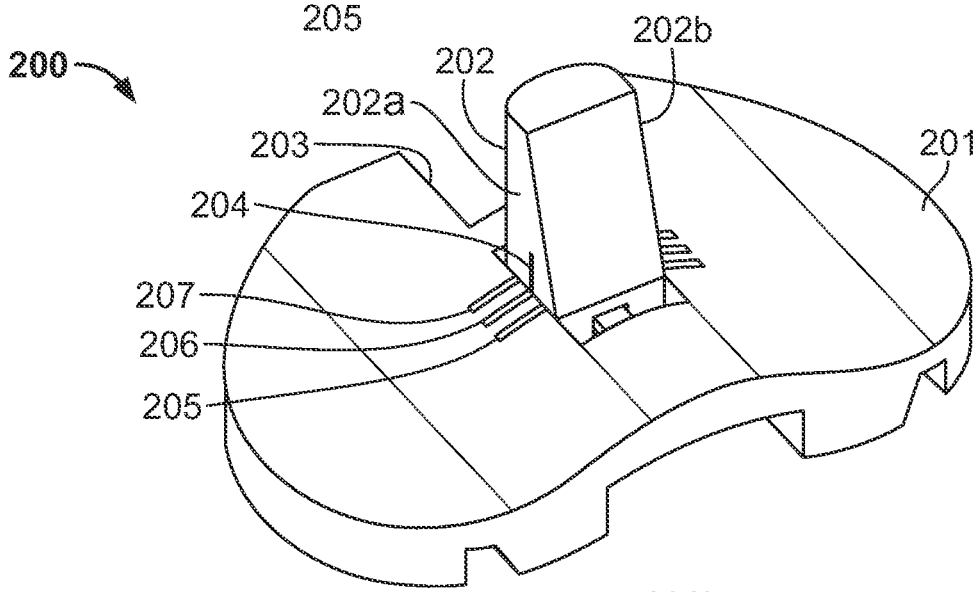
Figure 2C:
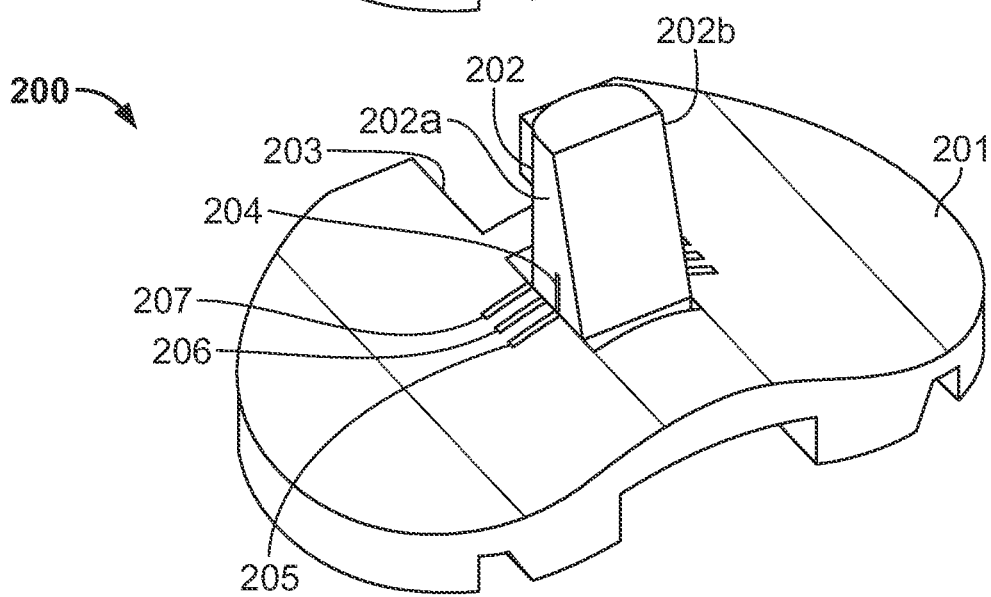

FIG. 2 shows an example of a permanent tibial insert 200 having an adjustably positionable posterior stabilizing post 202, similar to the post 102 of FIG. 1. The posterior stabilizing post 202 forms a right angle with the base 201. As with FIG. 1, the posterior stabilizing post of FIG. 2 can be coupled to a femoral component to stabilize the entire replacement joint, performing a function analogous to the posterior cruciate ligament (PCL). The anterior face of the posterior stabilizing post is slanted and the posterior face is vertical relative to the base. The posterior stabilizing post slides along the base and locks in place at desired locations relative to the base. FIG. 2A shows the posterior stabilizing post in the neutral position, which is a position that may be suitable for patients with normal soft tissue anterior to the joint. FIG. 2B shows the posterior stabilizing post in the anterior +2 position, indicating that the post is 2 mm anterior to the neutral position, which is a position that may be suitable for a patient having somewhat tight soft tissues anterior to the joint. In contrast, FIG. 2C shows the posterior stabilizing post in the anterior +4 position, indicating that the post is 4 mm anterior to the neutral position, which is a position that may be suitable for a patient having extremely soft tissues anterior to the joint. The posterior stabilizing post optionally comprises a post marking 204 that helps a user determine the position of the post at a glance. There may be post markings on both the lateral side 202a and medial side 202b, or on just one of the sides.

The base 201 abuts the posterior stabilizing post 202. The base is configured to be coupled to a tibial component so that the permanent insert 200 lies between the tibial component and the femoral component. The base preferably comprises a cruciate notch 203 through which the patient's anterior cruciate ligament (ACL) passes. The base optionally comprises several base markings 205, 206, and 207. When a user moves the posterior stabilizing post from one position to another, the post marking 204 lines up with one of the base markings (or falls between two base markings) so that the user can determine the position of the post at a glance. The posterior stabilizing post locks into place relative to the base strongly enough so the posterior stabilizing post does not move relative to the base when the patient engages in normal activity such as bending the knee, walking, and running. The permanent insert 200 may be used in the context of a joint implant.

Figure 3B:
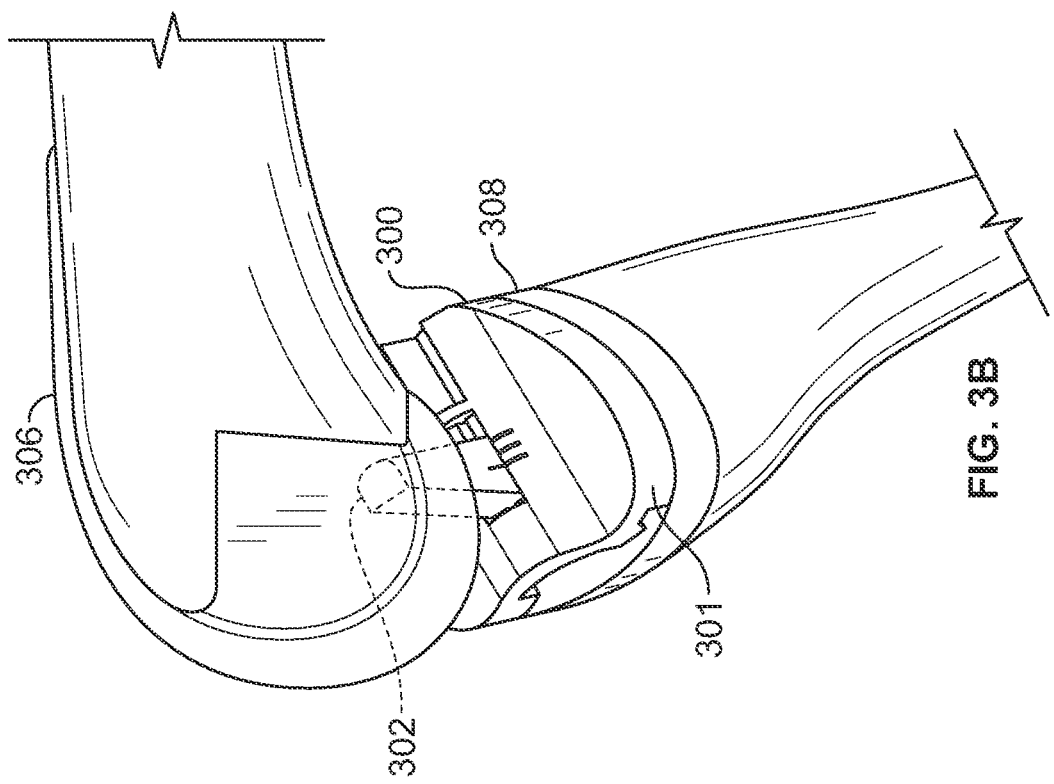
FIGS. 3A-D are side views of a replacement joint. The replacement joint comprises a permanent tibial insert with an adjustably positionable posterior stabilizing post. Panels A and B show the posterior stabilizing post in different positions along the anterior/posterior axis, resulting in different maximum rollback of the joint. Panels C and D show the relationship between the femoral component and the insert when the joint is flexed 135° (Panel C) or fully extended (Panel D).
Figure 3A:
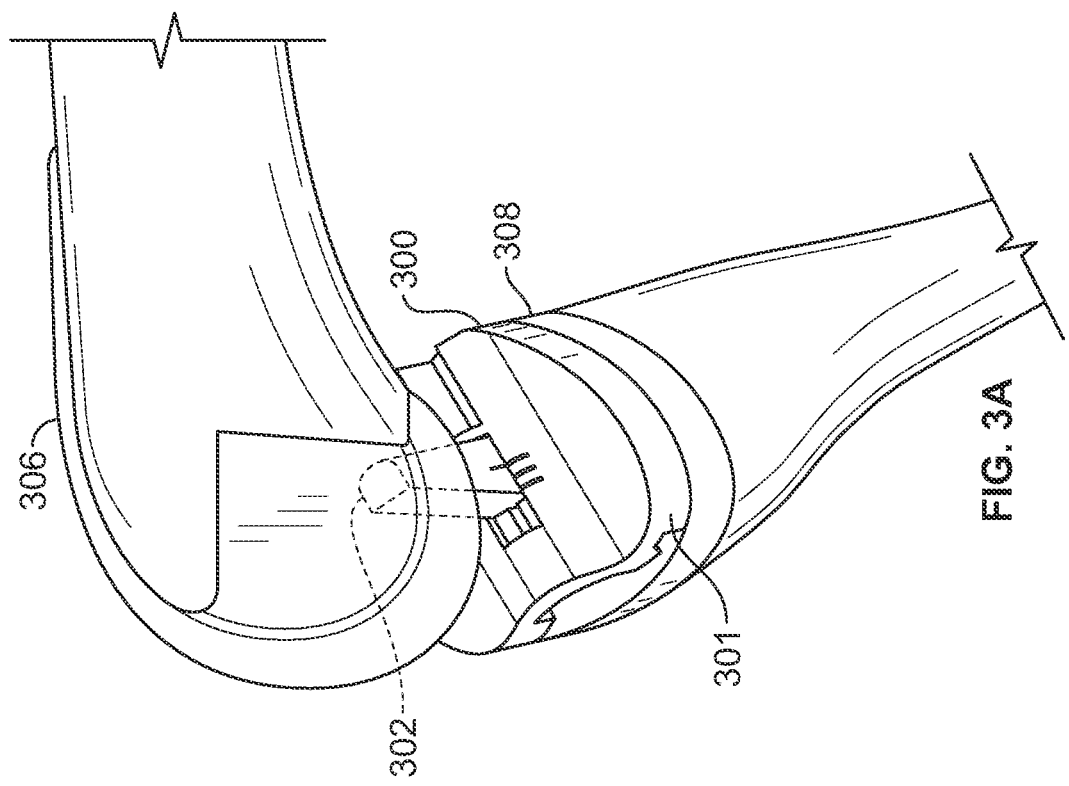
Figure 3C:
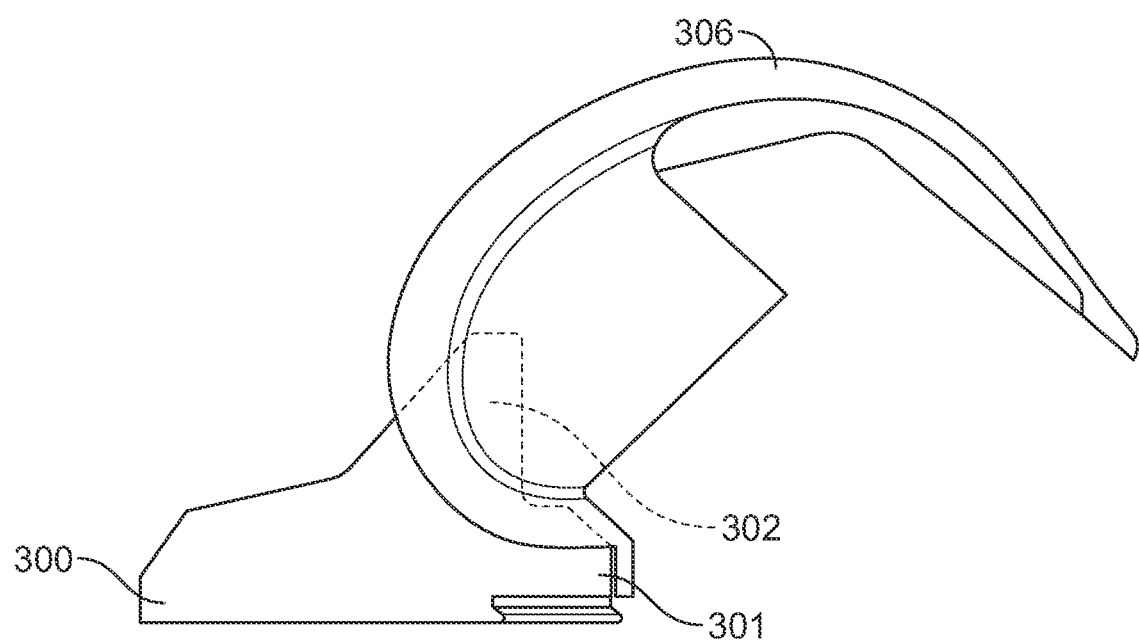
Figure 3D:
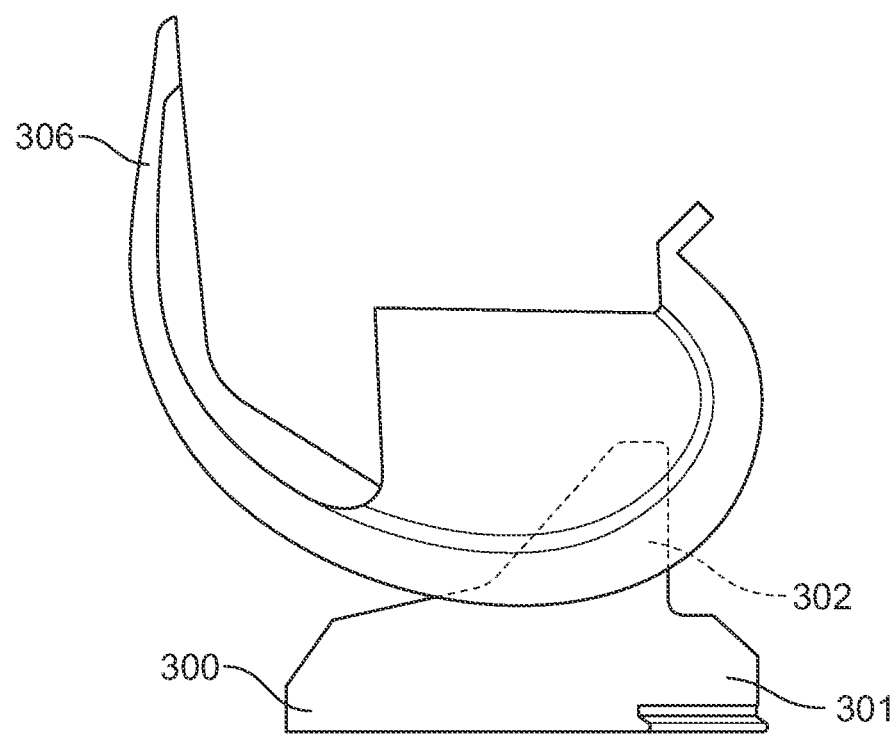

FIGS. 3A and B illustrate a permanent tibial insert in the context of a joint implant. The implant comprises a femoral component 306, a tibial component 308, and a permanent tibial insert 300. The insert is positioned between and coupled to the femoral component and the tibial component. The femoral component is immovably coupled to the patient's femur, and the tibial component is immovably coupled to the patient's tibia. The base of the permanent tibial insert attaches immovably to the tibial component. In contrast, the posterior stabilizing post of the permanent tibial insert is coupled to the femoral component in a manner that allows hinge-like motion, and this hinge motion allows the knee to flex and extend as shown in FIGS. 3C and 3D. FIG. 3C shows the joint implant flexed to 135°, and in FIG. 3D the joint implant is fully extended. In certain embodiments, the posterior stabilizing post passes through a hole in the femoral component. Because the femoral component prevents the post from translating anterior/posterior or medial/lateral directions, the post stabilizes the replacement joint and keeps the tibia and femur aligned with each other. However, any other suitable mechanism for creating a hinge-like connection may be used.

The permanent tibial insert 300 comprises a base 301 and a posterior stabilizing post 302. The posterior stabilizing post can be locked in the neutral position, as shown in FIG. 3A, or the +4 anterior position, as shown in FIG. 3B. The posterior stabilizing post can also be locked in other positions as described herein. When the posterior stabilizing post is in the neutral position, the knee is capable of greater rollback than when the posterior stabilizing post is in an anterior position. One example of a suitable permanent insert is the insert of FIG. 2.

Figure 4A:
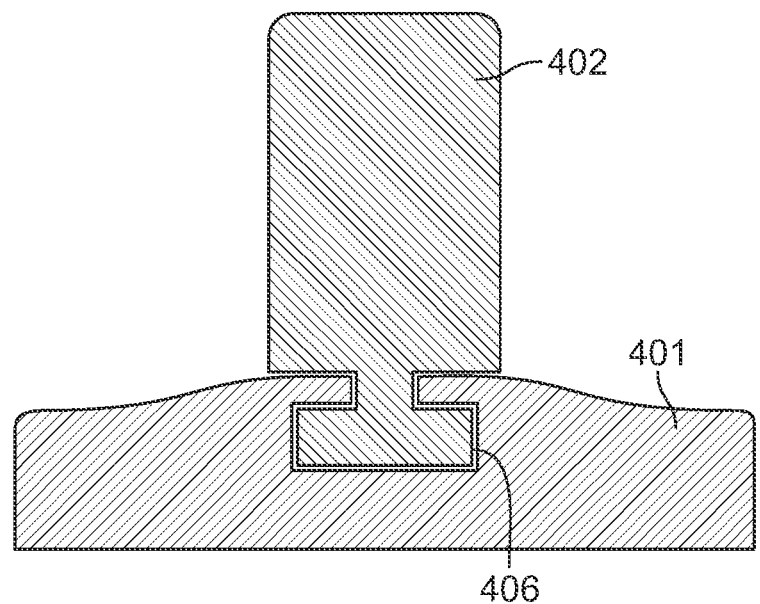
FIGS. 4A-D show cross-sectional views of a tibial insert with a posterior stabilizing post disposed in a trough. Panel A is a front cross-sectional view and Panels B-D are side cross-sectional views. Panels B-D show the posterior stabilizing post in different positions along the anterior/posterior axis.
Figure 4B:
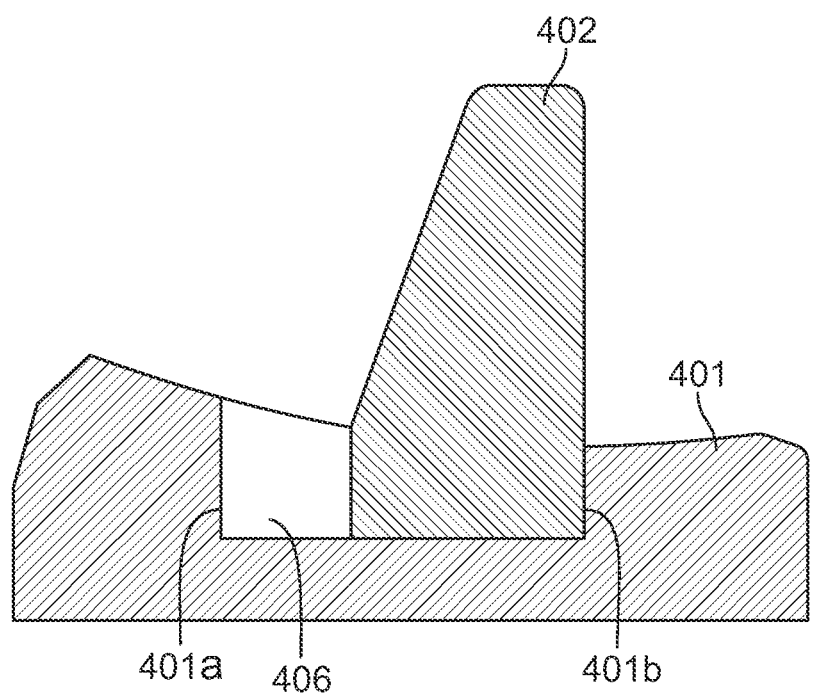
Figure 4C:
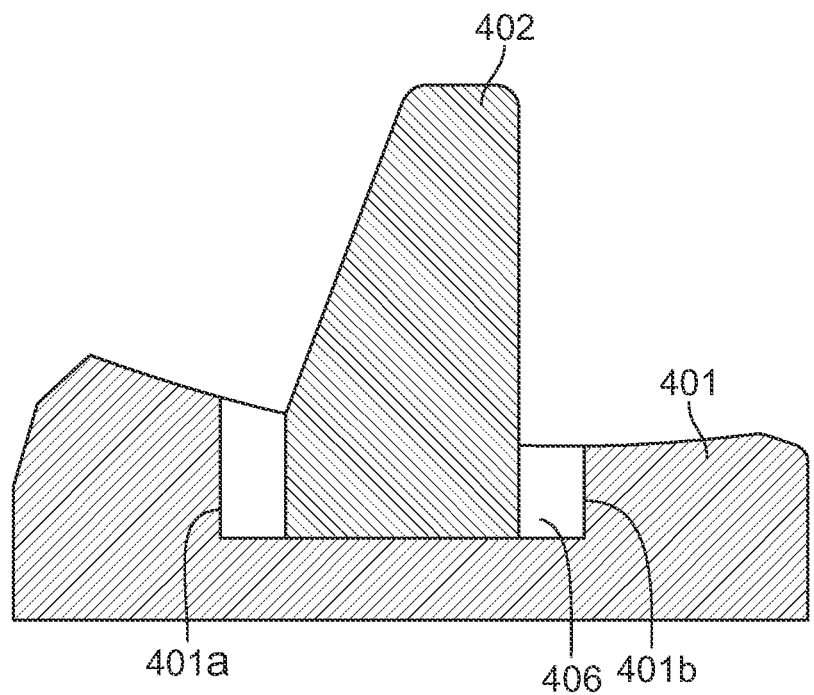
Figure 4D:
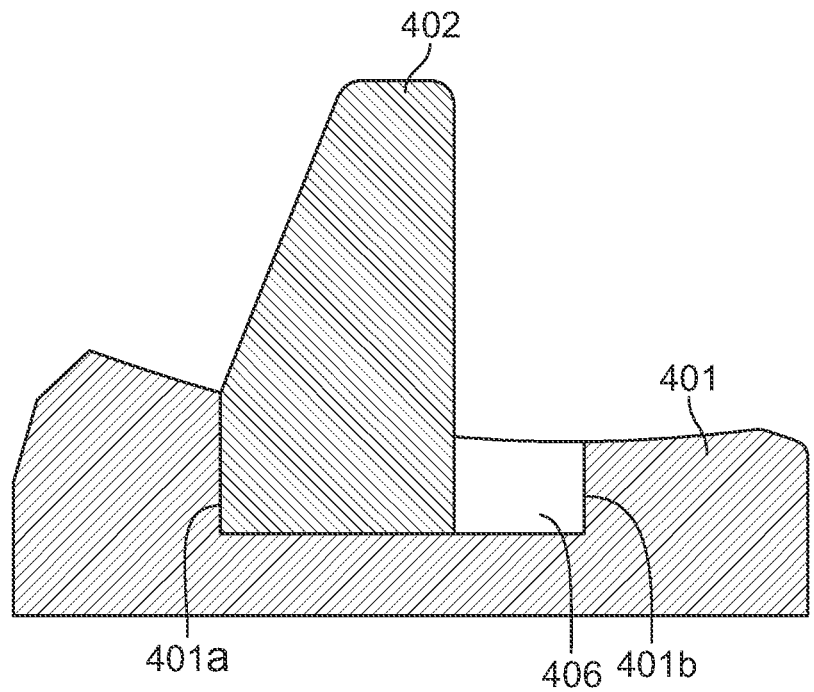
Figure 5:
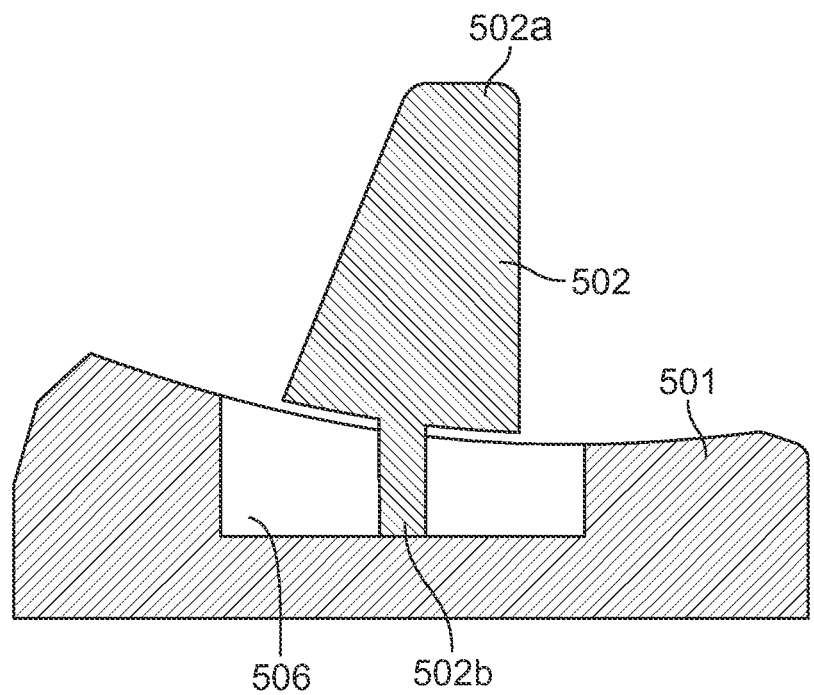
FIG. 5 is a cross-sectional view of a tibial insert where the portion of the posterior stabilizing post disposed within the trough is narrower than the portion of the post outside the trough.

Returning now to the tibial insert itself, the posterior stabilizing post can be coupled to a base, such as a tibial base, using various mechanisms. One such mechanism is illustrated in FIG. 4A. FIG. 4A shows a front cross-sectional view of an insert, wherein the base 401 has a trough 406 that extends anterior/posterior within the base, and the posterior stabilizing post 402 is disposed in the trough. The post slides within the trough 406. In contrast to FIG. 4A, FIGS. 4B-D shows side cross-sectional views of the insert. In FIG. 4B, the posterior stabilizing post 402 is disposed in the trough 406, and is in the neutral position relative to the base 401. In FIG. 4C, the posterior stabilizing post has been positioned in the +2 anterior position, and in FIG. 4D the posterior stabilizing post has been positioned in the +4 anterior position. The trough does not extend fully though the base, but ends with an anterior block 401a and a posterior block 401b that keep the posterior post from sliding out the anterior or posterior end of the base. These blocks could be, for example, a complete wall at the end of the trough as shown in FIGS. 4B-4D, so that the posterior stabilizing post is blocked from sliding out of the anterior or posterior end of the base. In other embodiments, the block is a small lip that is sufficient to stop the post from sliding out. Although in FIGS. 4B-D the part of the post disposed within the trough is virtually as wide as the part of the post immediately above the trough, the part of the post within the trough can also be larger or smaller. Such a post 502 is shown in FIG. 5. The post 502 has an upper portion 502a that is wider than its lower portion 502b. The post 502 is disposed in a trough 506 in the base 501 and can slide within the base. The post can be coupled to the base with various mechanisms including the arrangement shown in FIG. 4A. The part of the post within the trough should be large enough to give sufficient structural support, but small enough that it has room to slide within the trough. The trough mechanism of FIG. 4 can be used in a trial insert or a permanent insert.

Figure 6A:
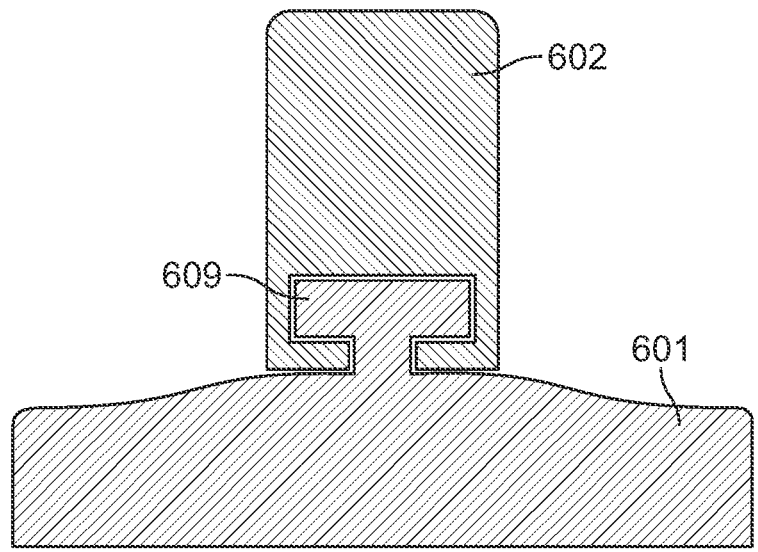
FIGS. 6A and B show a tibial insert with a posterior stabilizing post mounted on a rail. Panel A is the front cross-sectional view and Panel B is the side cross-sectional view.
Figure 6B:
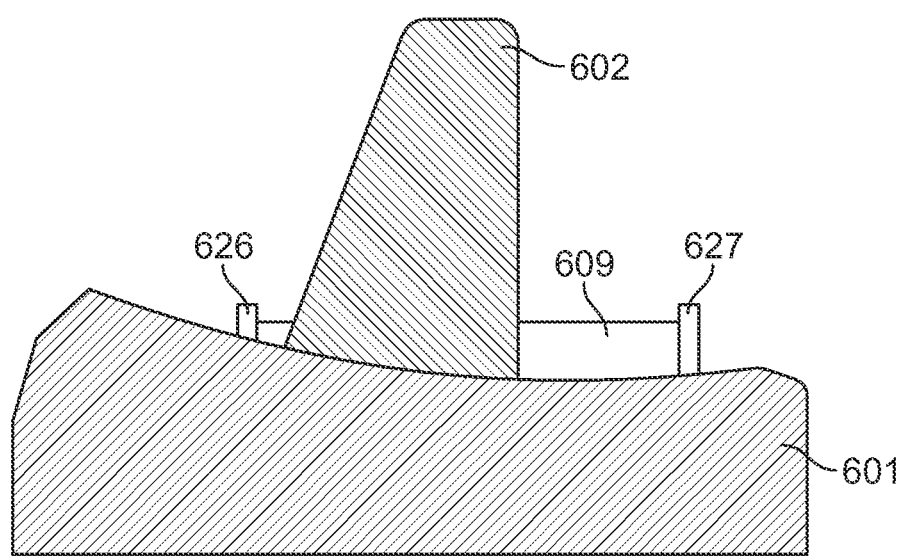

An additional mechanism for coupling the posterior stabilizing post to the base is depicted in FIG. 6. Instead of being disposed in a trough, as in FIGS. 4 and 5, the posterior stabilizing post 602 in FIG. 6 is mounted on a rail 609 that rises out of the base 601. The posterior stabilizing post can slide back and forth on the rail. FIG. 6A shows the front cross-section view of the rail-mounted post, and FIG. 6B shows the side cross-sectional view. The insert has an anterior block 626 and a posterior block 627 that keeps the posterior stabilizing post from falling off each end of the rail. The blocks 626 and 627 are raised ridge on the insert, positioned so that the posterior stabilizing post is blocked by the ridge from falling off the rail. However, other types of blocks may be substituted by those of skill in the art based on this disclosure. The rail mechanism of FIG. 6 can be used in a trial insert or a permanent insert.

A trough and a rail are examples of mechanisms for coupling the post to the base in a manner that allows sliding. One of skill in the art will readily appreciate from this disclosure that other sliding coupling mechanisms are available.

Figure 7:
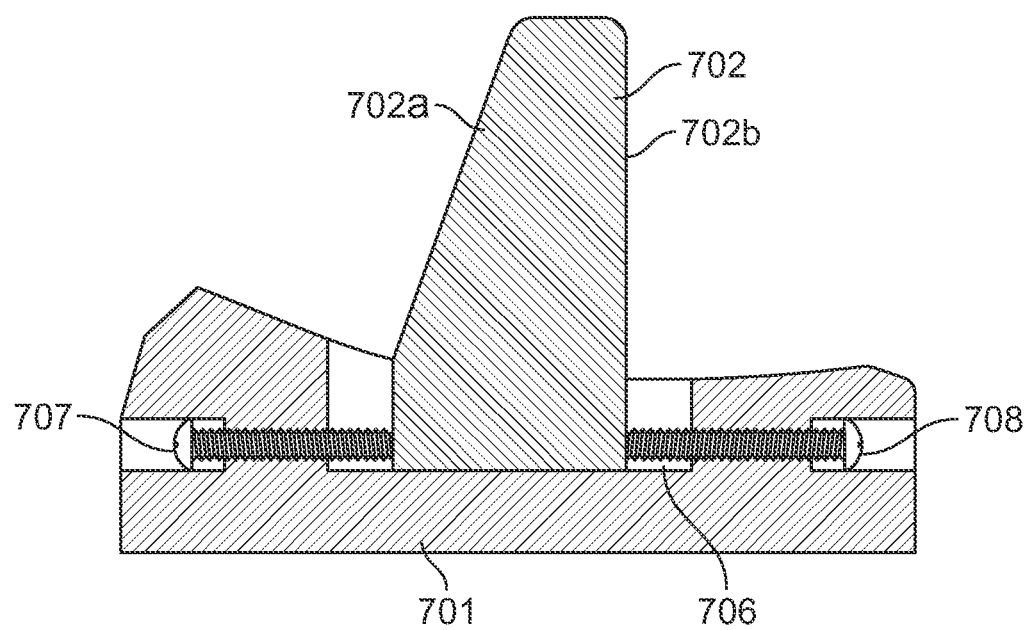
FIG. 7 is a side cross-sectional view of a tibial insert with a posterior stabilizing post that locks in place with paired screws.

Locking inserts can be used to lock the posterior stabilizing post relative to the base. FIG. 7 illustrates one locking insert for locking a post relative to a tibial insert base. In this side cross-sectional view, paired screws 707 and 708 lock the posterior stabilizing post 702 in place relative to the base 701. A user can turn the screws to position the posterior stabilizing post at any position within the trough 706. By turning the paired screws, a user may lock the post in any desired position within the trough. FIG. 7 shows the posterior stabilizing post in the +2 anterior position, but the post could also be locked at, e.g., the +1 position, the +0.5 position, or other suitable positions. To lock the post in place, the user tightens the screws until the anterior screw 707 exerts force directly or indirectly on the anterior face 702a of the posterior stabilizing post and the posterior screw 708 exerts force directly or indirectly on the posterior face 702b of the posterior stabilizing post. The screw exerts force directly if it is in direct contact with the post, and exerts force indirectly if there is another component between the post and the screw.

Figure 8A:
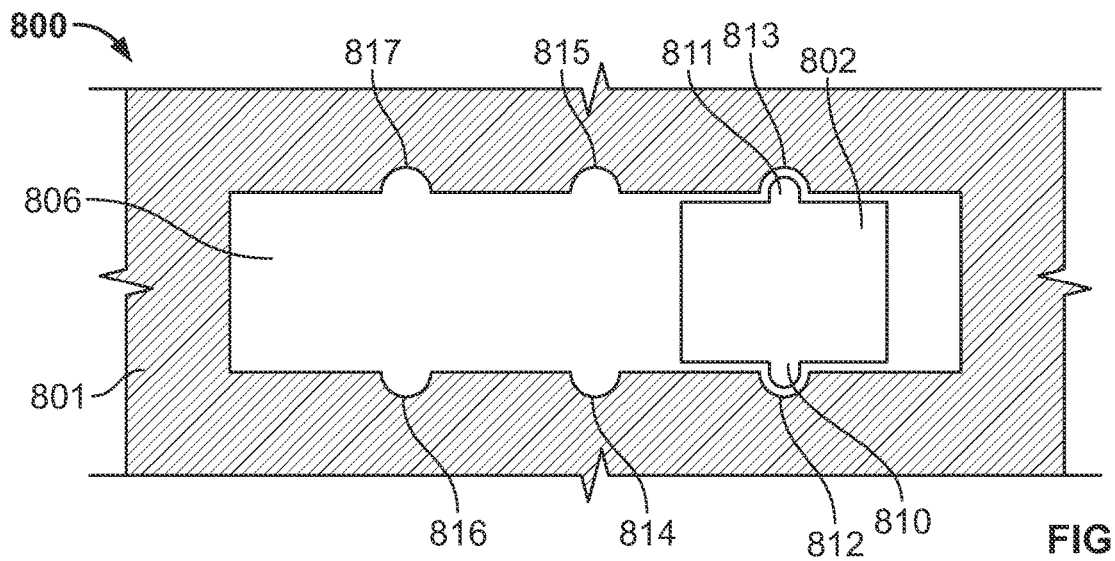
FIGS. 8A-C are side cross-sectional views of a tibial insert with a posterior stabilizing post that locks in place with a ball and detent system. Panels A-C show the posterior stabilizing post in different positions along the anterior/posterior axis.
Figure 8B:
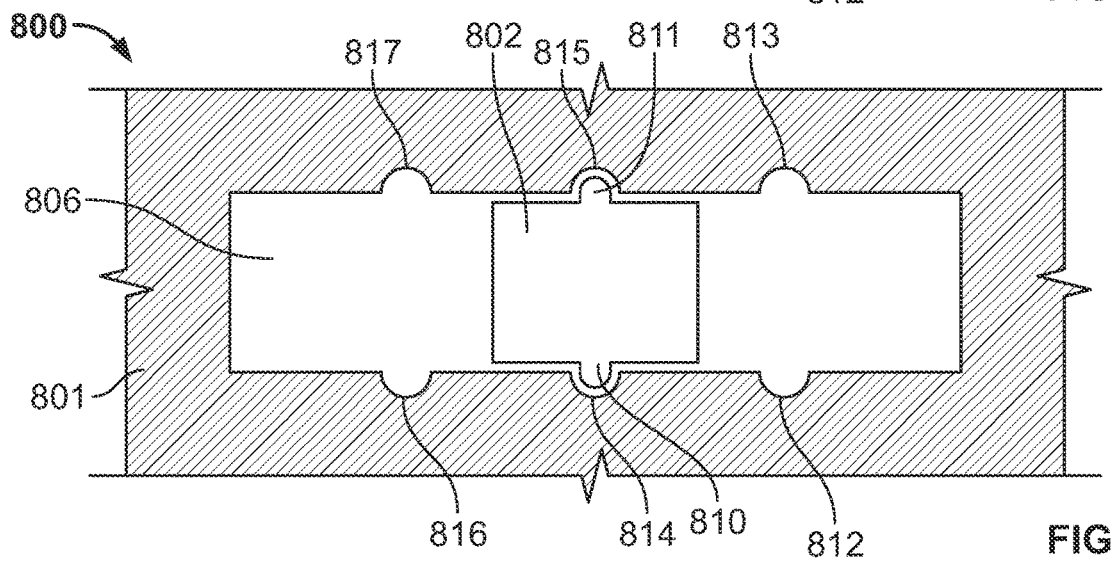
Figure 8C:
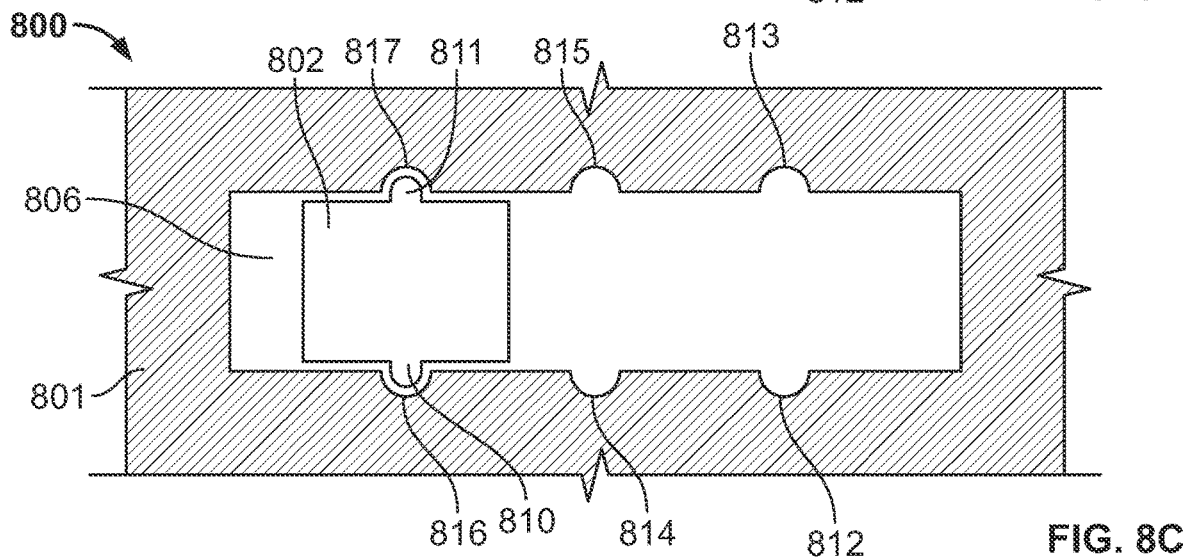

Another locking insert is illustrated in FIG. 8. The tibial insert of FIG. 8 uses a ball-and-detent system that allow a user to position the posterior stabilizing post 802 into one of several discrete locations. Unlike the paired screw mechanism of FIG. 7, which allows a user to lock the post into place in any desired position, the ball and detent system of FIG. 8 locks the post in positions defined by the detents. More particularly, FIG. 8 depicts top cross-sectional views of the insert 800, looking down at the base 801 into the trough 806. In FIG. 8A, the posterior stabilizing post is in the neutral position and its left ball 810 and right ball 811 are disposed in the left posterior detent 812 and a corresponding right posterior detent 813. In FIG. 8B, the posterior stabilizing post is in the +2 anterior position and its left ball 810 and right ball 811 are disposed in the left central detent 814 and a corresponding right central detent 815. In FIG. 8C, the posterior stabilizing post is in the +4 anterior position and its left ball 810 and right ball 811 are disposed in the left anterior detent 816 and a corresponding right anterior detent 817. A user can adjust the posterior stabilizing post from one position to another by pushing on the post, thereby mechanically forcing the balls 810 and 811 out of their respective detents, e.g., 812 and 813. The balls 810 and 811 are large enough to frictionally hold the posterior stabilizing post in place firmly with the detents so that a patient's normal motion will not move the posterior stabilizing post from one location to another. However, the balls 810 and 811 are small enough that a user can snap the posterior stabilizing post to a different position before or during knee replacement surgery. Another example of a locking insert is similar to the ball and detent system in FIG. 8, but the balls are retractable. The user retracts the balls to unlock the post, and re-extends the balls into detents in the base to lock the post again.

Figure 9A:
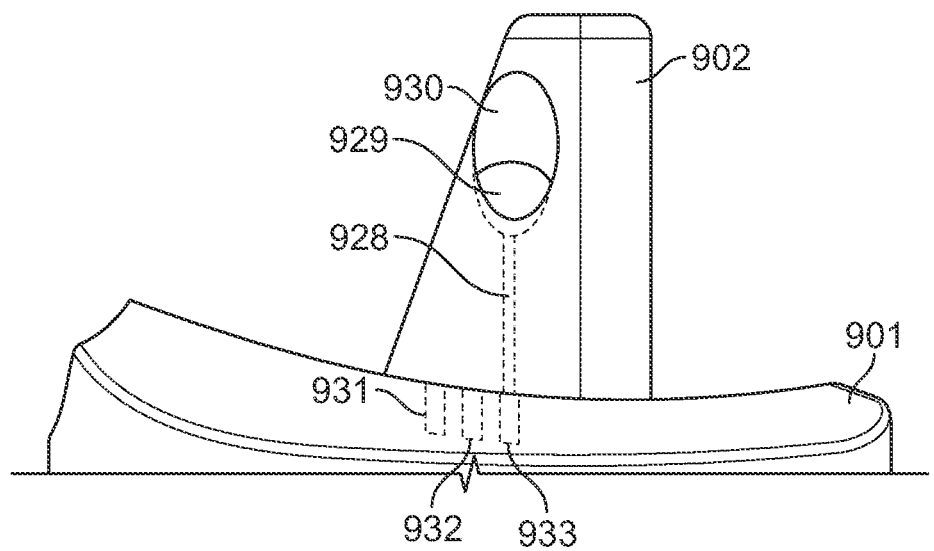
FIGS. 9A and B are side cross-sectional views of a tibial insert with a posterior stabilizing post that locks in place with a locking tab. Panel A shows the post locked in place, and Panel B shows the post unlocked.
Figure 9B:
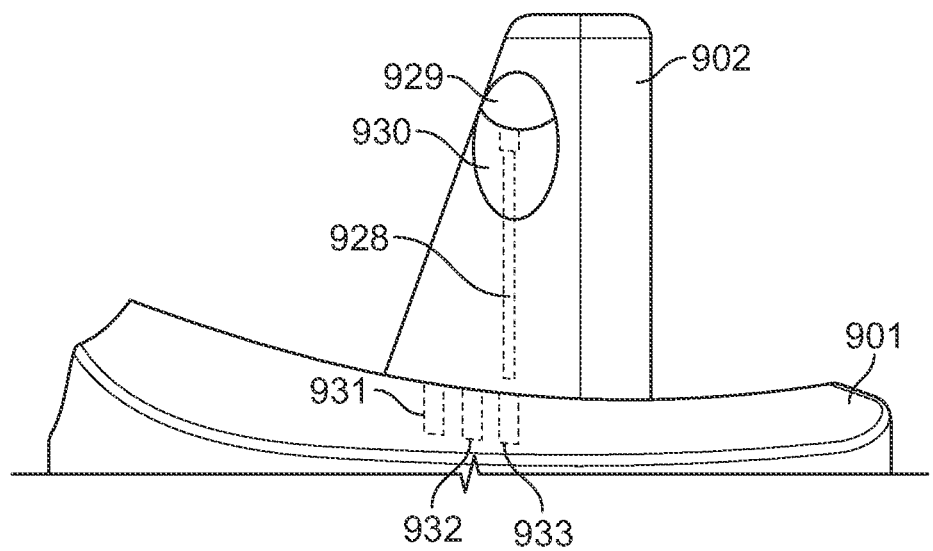

The locking inserts of FIGS. 7 and 8 are illustrative only. One of skill in the art will be able to implement other locking inserts based on a review of this disclosure. An example of another locking insert is a locking tab, shown in FIG. 9. A locking tab system includes a vertical rod 928 disposed within the posterior stabilizing post. The top of the locking tab 929 is exposed and accessible via an access window 930 so the user can move the locking tab up or down. The bottom of the locking tab can fit into one of several locking wells 931, 932, and 933. To move the posterior stabilizing post, the user lifts the locking tab 928, slides the posterior stabilizing post 902 to the desired position, and then locks the post in place by pushing the locking tab 928 into one of the locking wells 931, 932, or 933. FIG. 9A shows the locking tab 928 disposed within the posterior locking well 933 so that the post 902 is locked. FIG. 9B, in contrast, shows the post 902 unlocked because the locking tab 928 is not disposed within any locking well.

When a post is locked in place, it remains in a fixed position relative to the base during normal flexion and rollback of the knee. Locking is not final; a user can unlock the post and move it to a new position before or during surgery.

The locking inserts of FIGS. 7-9, as well as the other locking inserts described herein, can be used with a trial insert or a permanent load-bearing insert.

This disclosure also describes a tibial insert with a posterior stabilizing post that slides relative to the base, and compresses or extends a spring or other resistance member as it slides. FIG. 10 shows such a spring-actuated insert 1000, including a posterior stabilizing post 1002 and a base 1001. The posterior stabilizing post is coupled to the base using a mechanism, for example a trough or rail, that allows the post to slide relative to the base. When the post slides relative to the base, it compresses a spring 1015 or other resistance member disposed within the base 1001.

Figure 10A:
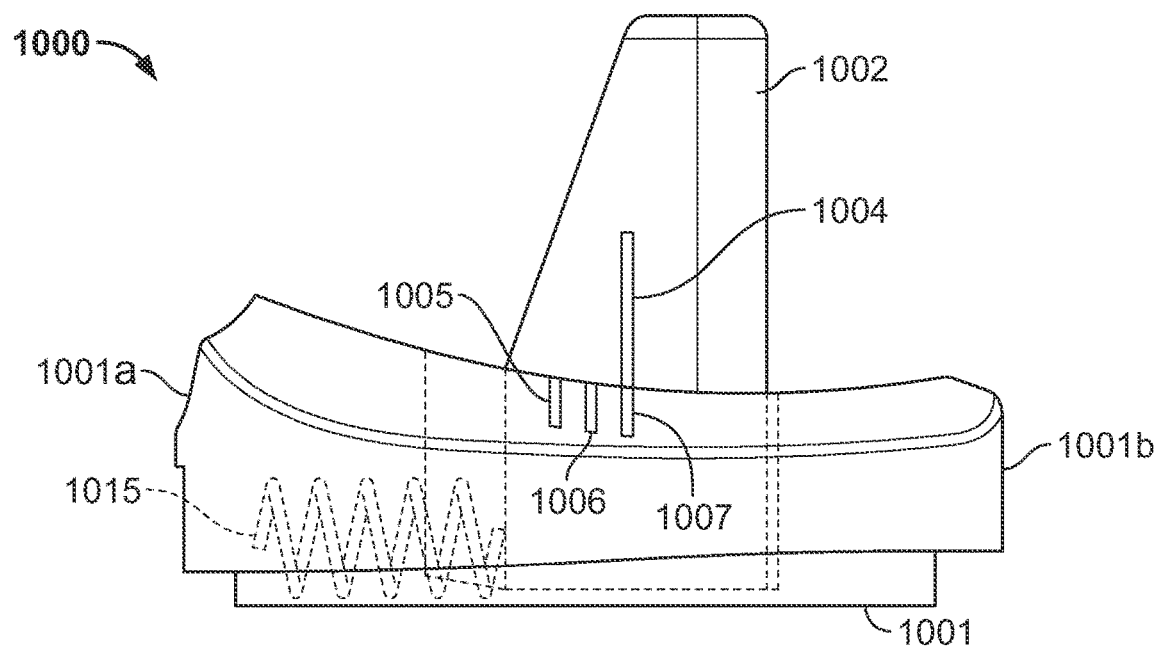
FIGS. 10A-G show cross-sectional views of a trial insert with a moveable posterior stabilizing post. Panels A-D show side cross-sectional views of the trial insert. Panels A-C show the posterior stabilizing post in different positions along the anterior/posterior axis. Panel D is a cut-away side view of the trial insert with the posterior stabilizing post in the neutral position. Panel E is a top cross-sectional view of the trial insert with the posterior stabilizing post in the neutral position. Panels F and G show the relationship between the femoral component and the insert when the joint is fully extended (Panel F) or flexed 135° (Panel G).
Figure 10B:
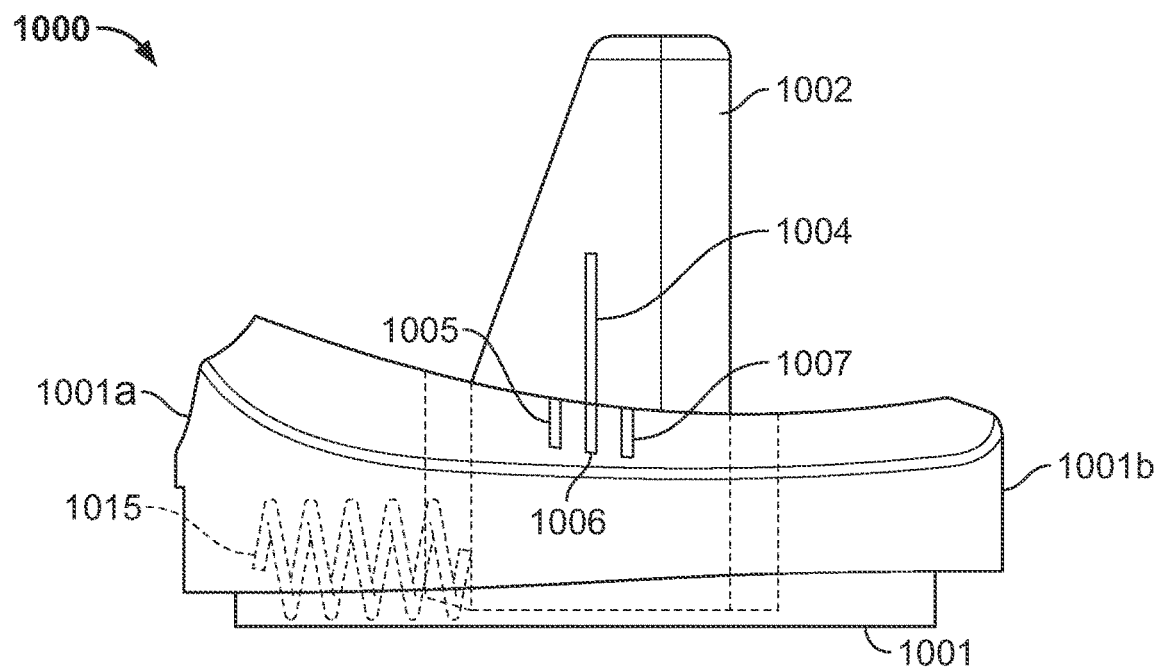
Figure 10C:
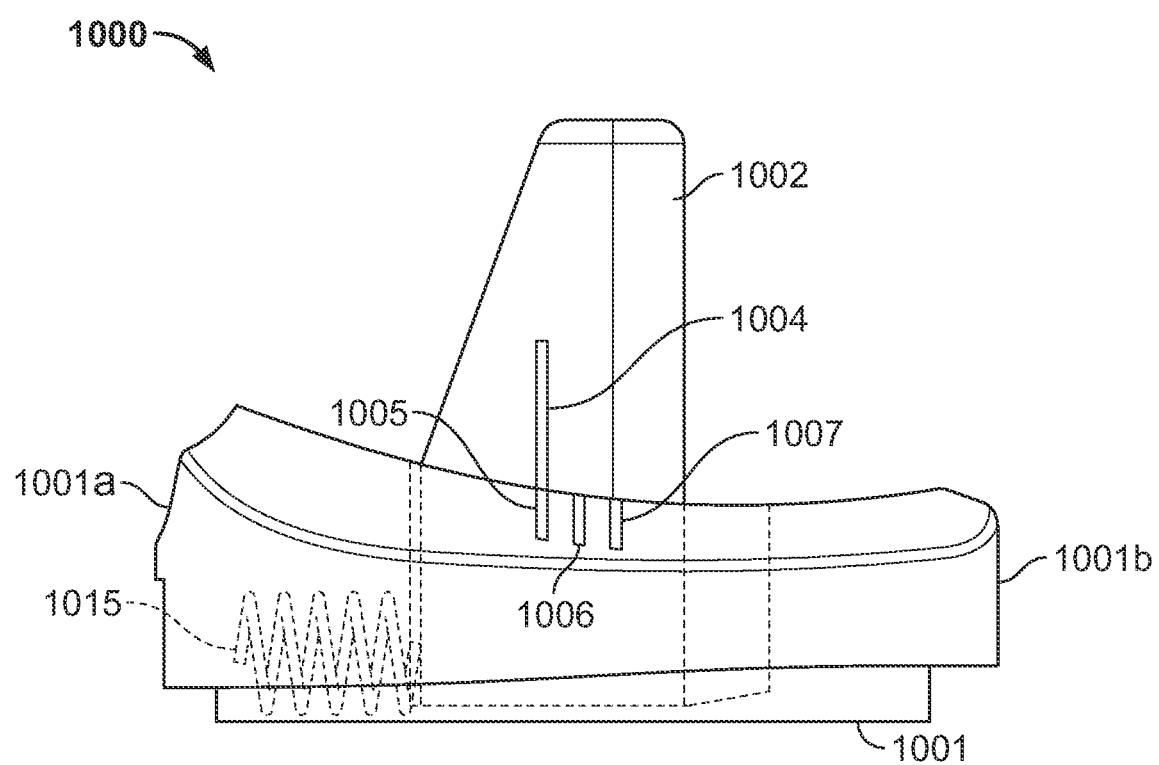

The spring 1015 is positioned anterior to the post, so that the spring compresses when the post slides towards the base's anterior end 1001a, and extends when the post slides towards the base's posterior end 1001b. Preferably, the post slides smoothly from one position to another, without locking. FIG. 10A shows the posterior stabilizing post in the neutral position, FIG. 10B shows it in the +2 anterior position, and FIG. 10C shows it in the +4 anterior position. The spring 1015 is most extended in FIG. 10A when the posterior stabilizing post is in the neutral position, and the spring is most compressed in FIG. 10C when the posterior stabilizing post is in the anterior position. In certain embodiments, the insert comprises exactly one spring.

Other resistance members can be used in place of a spring. The resistance member may be made from a material that is compressible and resilient. For instance, one can use a solid length of compressible and resilient material, such as a biocompatible elastic, rubber, or foam. The resistance may be controlled by the choice of material as well as the size and shape of the resistance member. In some embodiments, the resistance member extends from the lateral wall to the medial wall of the trough, and in other embodiments it only extends a portion of this distance. In some embodiments, the resistance member extends from the bottom of the trough to the top of the trough; in other embodiments, it only extends a portion of this distance.

Furthermore, a resistance member may be chosen from several types of spring. For example, the resistance member may be a cylindrical spring or a leaf spring.

Because the resistance member presses against the posterior stabilizing post, the insert provides force feedback during the joint's range of motion. This motion is shown in the context of a femoral component and insert in FIGS. 10F and 10G. FIG. 1OF shows a fully extended joint, and FIG. 10G shows a joint flexed 135°. As the patient's knee flexes, the cam 1035 of the femoral component 1034 engages the insert's posterior stabilizing post, causing the post 1002 to move anteriorly. The cam can simply be the portion of the femoral component directly posterior to the post. In some embodiments, the cam is a rod extending between the femoral component's condyles. The force of the cam 1035 is illustrated as the arrow $F_c$ in FIGS. 10F and 10G. As the post moves anteriorly, the spring 1015 begins to resist, exerting force on the post in the posterior direction. The force of the spring 1015 is illustrated as the arrow $F_s$ in FIGS. 10G and 10G. Preferably, the post comes to a rest when the anterior cam force $F_c$ equals the posterior force exerted by the spring $F_s$.

In some embodiments, the resistance member is affixed to the base. There are several appropriate methods for doing so. For instance, if the resistance member is metal, it may be welded to the base using a non-toxic welding material. As another example, the resistance member may be glued to the base using a durable, biocompatible glue.

To help the user determine the position of the posterior stabilizing post, the post 1002 optionally has a post marking 1004. The base 1001 optionally has base markings 1005, 1006, and 1007. The user can tell at a glance the position of the post marking relative to the base markings.

Figure 10D:
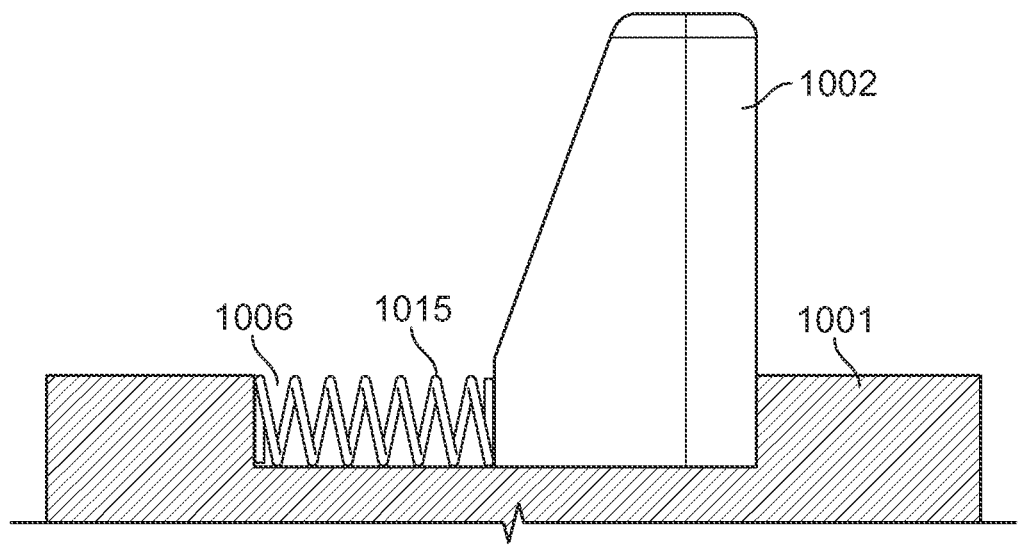
Figure 10E:
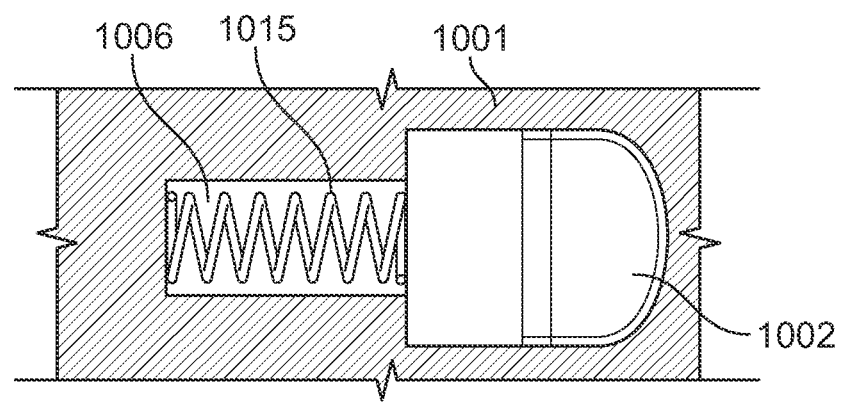
Figure 10F:
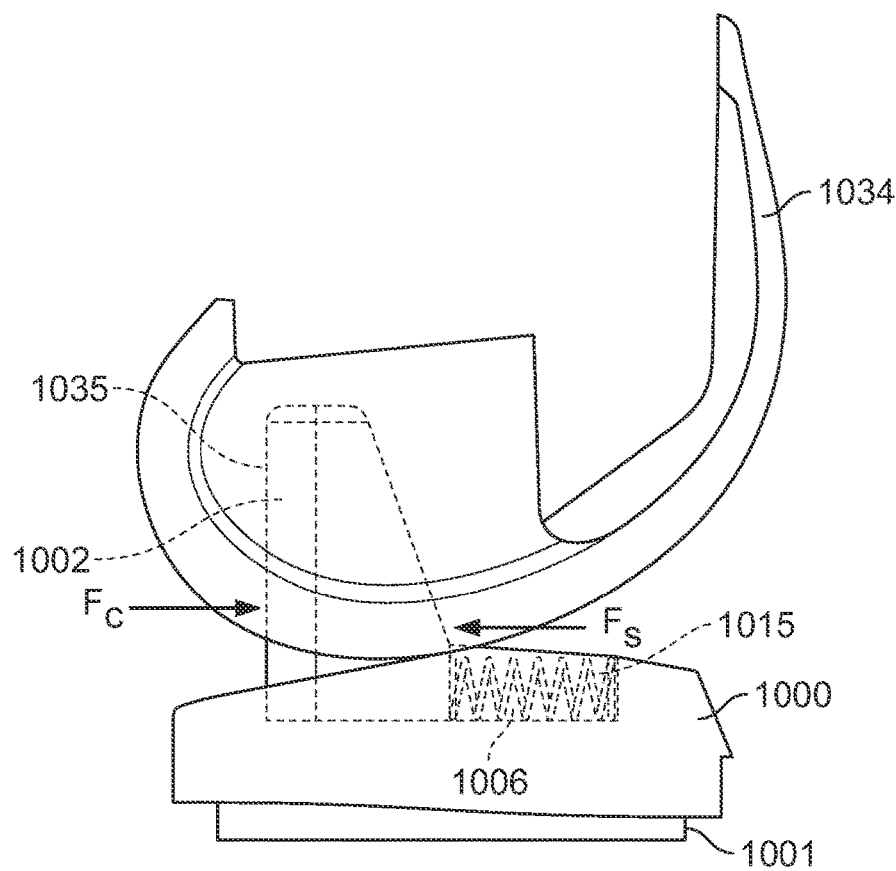
Figure 10G:
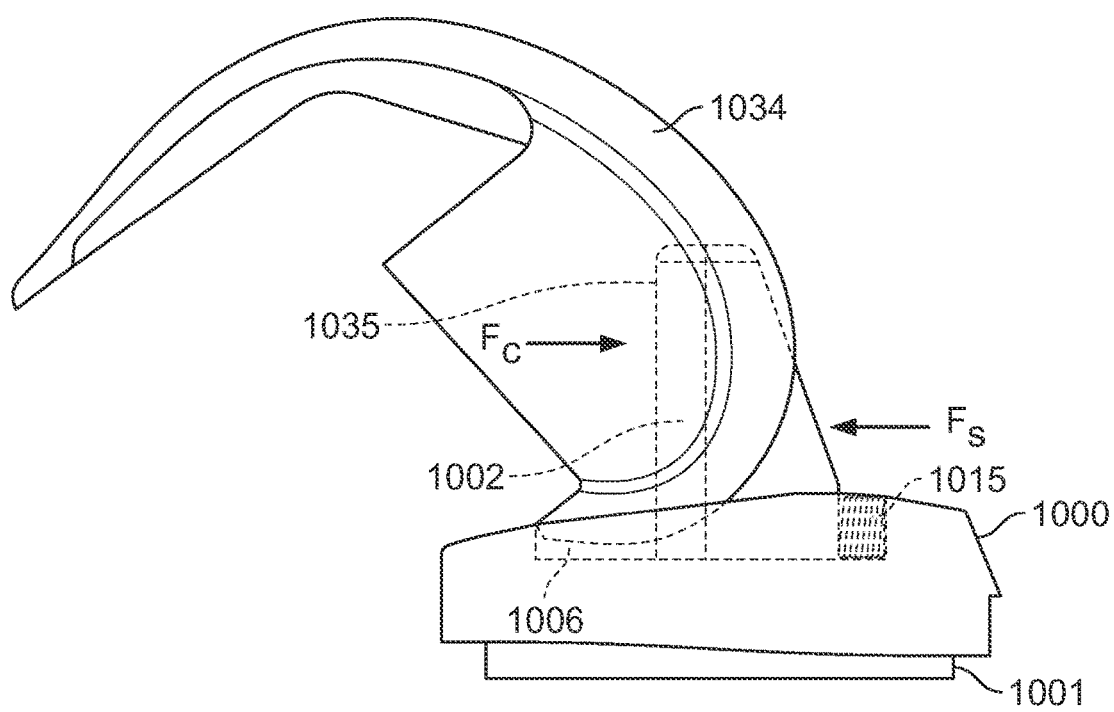

FIGS. 10D and 10E show the spring-actuated insert in cross-sectional views. FIG. 10D shows a side cross-sectional view of the posterior stabilizing post 1002 in its neutral position, contacting an extended spring 1015. Both spring and post are disposed in a trough 1006 in the base 1001. FIG. 10E shows a top cross-sectional view, looking down at the posterior stabilizing post 1002 in its neutral position. The post contacts an extended spring 1015. Both spring and post are disposed in a trough 1006 in the base 1001.

Although FIG. 10 shows a spring disposed within a trough in a base, one can use other mechanisms to modulate the posterior stabilizing post's sliding relative to the base. For instance, the post may be mounted on a rail as shown in FIG. 6. In this case, the resistance member (e.g., a spring) could lie just above the base. One end of the resistance member would contact the post, and the other end of the resistance member would be affixed to a support rising from the base.

In certain embodiments, the insert of FIG. 10 is configured as a trial insert. A user can then observe the position of the trial insert's posterior stabilizing post 1002 relative to the base 1001 when the patient's knee is flexed to different extents, including enough flexion to observe rollback. The user can determine a desired location of the post based on the evaluations of the fit, taking into account considerations such as whether the position of the post allows sufficient rollback of the knee and whether the soft anterior tissues are unduly stretched during rollback. Based on this determination, the user can select a permanent insert with a post in the desired position. Typically, the resistance member is designed to have compressibility and resilience such that the desired position of the post is the position in which the post comes to rest as the user flexes the patient's knee. In some embodiments, where the resistance member is a spring, the spring may have a spring constant such that the desired position of the post is the position in which the post comes to rest as the user flexes the patient's knee.

The insert of FIG. 10 can also be configured as a permanent insert. An insert comprising a resistance member provides a patient with a number of benefits compared to an insert with a fixed post. Because soft joint tissue structures vary from patient to patient, customizing the post's anterior/posterior sliding range may allow a range of motion tailored to the patient. In addition, using a resistance member to cushion the post's motion makes joint flexion feel more natural to a total knee arthroplasty patient.

Figure 11A:
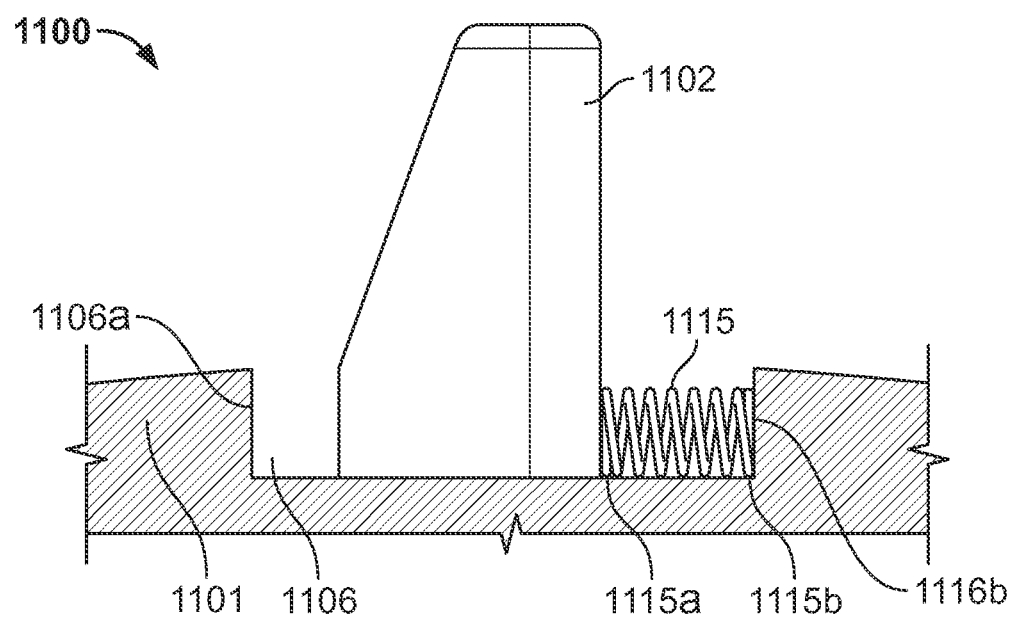
FIGS. 11A-B show a trial insert with the spring posterior to the post.
Figure 11B:
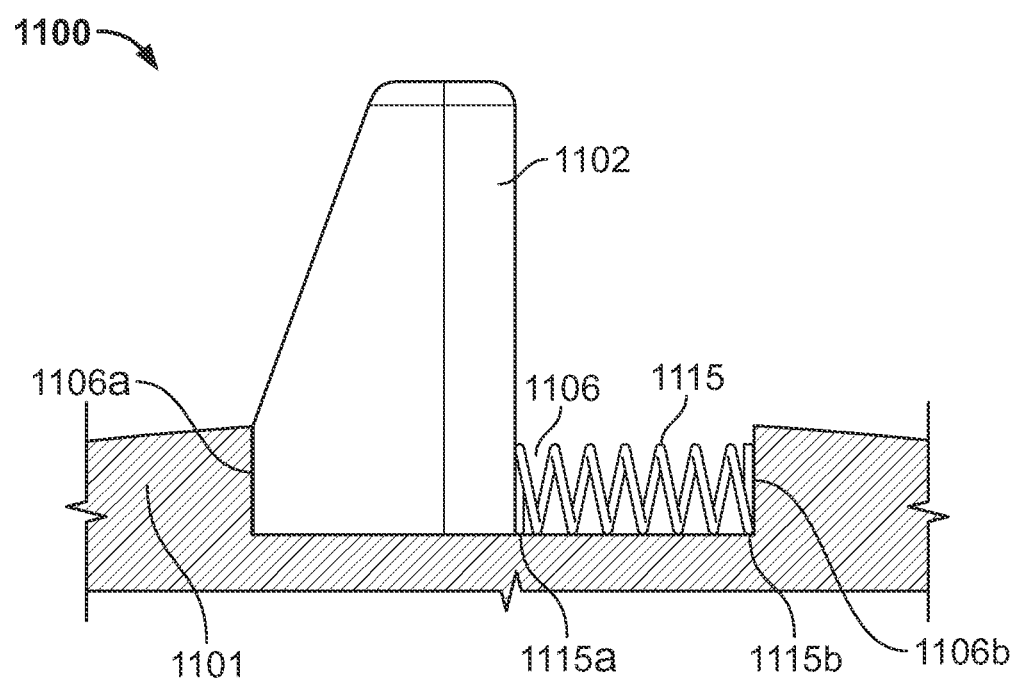

Although FIG. 10 shows the spring positioned anterior to the post, other arrangements can be used. For instance, the spring or other resistance member can be situated in the trough posterior to the post. FIG. 11 illustrates this arrangement. The insert 1100 has a base 1101 and a posterior stabilizing post 1102 disposed within a trough 1106 in the base 1101. The spring 1115 is posterior to the post 1102, with the anterior end of the spring 1115a situated against the post 1102 and the posterior end 1109b of the spring 1109 against the posterior end 1106b of the trough. The length of resistance member is chosen so that when the resistance member is substantially relaxed, the post is in its most posterior position, as shown in FIG. 11A. As the post is pushed towards the anterior end 1106a of the trough, as shown in FIG. 11B, the resistance member stretches and resists the anterior motion of the post. Furthermore, in some embodiments, there is a resistance member (e.g., a spring) to the anterior of the post and another resistance member (e.g., a spring) to the posterior of the post.

Although the Figures show the posterior stabilizing post moving between the neutral, +2 and +4 anterior positions, the inserts can also be designed to allow the post to move in other directions and be positioned at other locations. For example, the post could move or be positioned past the +4 anterior position to, e.g., the +5 or +6 positions. As another example, the post could move or be positioned posterior to the neutral position to, e.g., the −2 or −4 posterior position. The insert can also be designed such that the post moves or can be positioned along a medial/lateral axis instead of or in addition to an anterior/posterior axis.

This disclosure provides trial inserts and permanent inserts. Trial inserts, such as the insert 100 of FIG. 1, allow a user to place the insert in a patient during joint replacement surgery, test the joint rollback when the posterior post is in different positions, remove the trial insert from the knee, and select an appropriate permanent insert based on the fit of the trial insert. A trial insert is preferably made of a material that is non-toxic. Because a trial insert is typically only in the body for minutes or hours, the trial insert is preferably made of a material suitable for short-term patient contact. The trial insert can, but need not, be strong enough to support the patient's weight.

Permanent inserts, such as the insert 200 shown in FIG. 2, can be implanted into a patient's joint and remain there and support the patient's weight for a prolonged period of time such as at least 1, 2, 3, 4, or 5 or more years. A permanent insert can be removed and replaced in a subsequent joint replacement surgery. A permanent insert is preferably made of a biocompatible material. A permanent insert is also preferably load-bearing, i.e., having sufficient strength to support a patient's weight and sufficient durability to last for several years in the patient's body.

For the trial inserts and permanent inserts disclosed herein, any biocompatible material may be used, including but not limited to stainless steels, titanium and its alloys, cobalt-chrome and its alloys, cobalt chromium molybdenum alloy (Co—Cr—Mo), titanium alloy (Ti-6Al-4V), ultra-high molecular weight polyethylene (UHMWPE), ceramics, composite materials, polymers, and any other suitable materials and any combinations thereof. Other examples include, but are not limited to, titanium carbide, titanium nitride, ion-implantation of titanium, diffusion hardened metals, diamond-like coatings, diamond-like carbon, zirconium nitride, niobium, oxinium or oxidized zirconium, ceramics such as alumina and zirconia, and many other biocompatible materials and coatings. Any of the components disclosed herein may include surface treatments or additives in one or more of the component materials to provide beneficial effects such as anti-microbial, analgesic or anti-inflammatory properties.

Any of the trial inserts disclosed herein may be made of materials suitable for short-term patient contact. Suitable materials include biocompatible metals or metal alloys including stainless steel, cobalt chrome, titanium alloy; plastics including polyetherimide, polypropylene, acetal, polycarbonate, polyetheretherketone (PEEK) and any other suitable materials and any combinations thereof. Reinforcing materials such as glass fiber or carbon fiber can be added to, for example, embodiments comprising plastic, to add strength and dimensional stability. Preferably, a trial insert is made of a material suitable for sterilization.

The inserts disclosed herein may be formed in varying footprint shapes including ovoid, rectangular, circular, square, polygonal, and may be bilaterally symmetrical from a medial-lateral, superior-inferior, and/or anterior-posterior perspective, or bilaterally asymmetrical from one or more of those perspectives. Typically, the footprint of the insert will be similar to the footprint of the tibial component so that the insert's base can be conveniently coupled to the tibial component.

Figure 12:
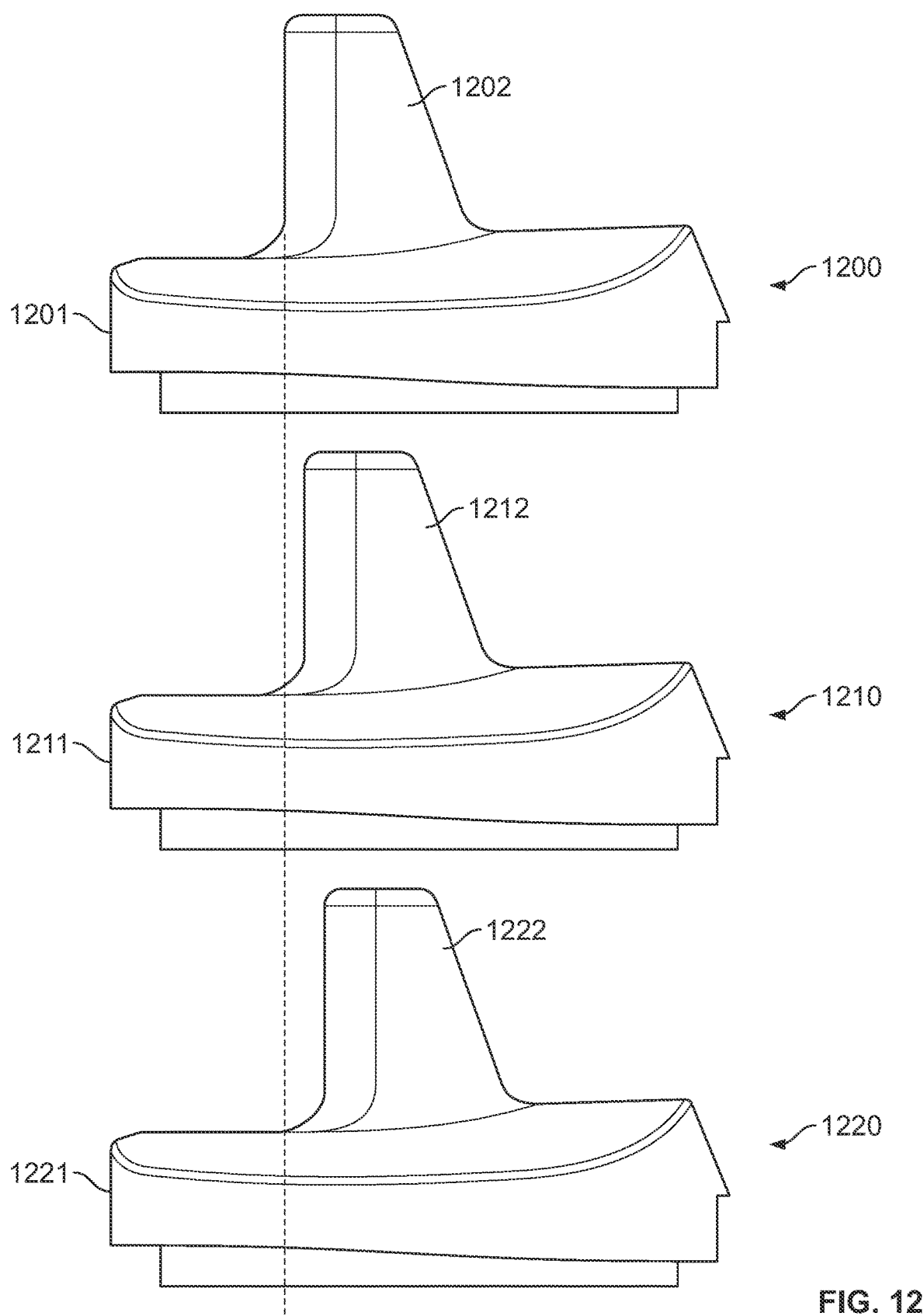
FIG. 12 shows three trial inserts. Each insert has an immovable posterior stabilizing post in a different position along the anterior/posterior axis.

FIG. 12 shows a set of trial inserts that can be used to select an appropriate permanent insert. These trial inserts 1200, 1210, and 1220 each have a posterior stabilizing post 1202, 1212, and 1222 that is immovably coupled to the base 1201, 1211, and 1221. The post and base are immovably coupled in the sense that their relative positions can not be changed during the life of the trial insert. In some embodiments, the post and base are one contiguous object produced in a single mold for ease of manufacture.

The dotted vertical line in FIG. 12 is a visual aid that illustrates the position of each posterior stabilizing post relative to the neutral position. The posterior stabilizing post 1202 of the first trial insert 1200 is coupled to the base 1201 at the neutral position. The posterior stabilizing post 1212 of the second trial insert 1210 is coupled to the base 1211 at the +2 anterior position. The posterior stabilizing post 1222 of the third trial insert 1220 is coupled to the base 1221 at the +4 anterior position. Each trial insert in FIG. 12 allows a different amount of rollback.

Rollback describes a type of motion that a joint undergoes when the joint is almost fully flexed. For approximately the first 75° of knee flexion, no rollback occurs, and the distal end of the femur contacts a constant region of the tibia. After the first 75° of flexion, the contact point between the femur and the tibia moves to the posterior of the tibial surface; this is rollback. Thus, joint inserts with posts in different positions allow different amounts of rollback. In particular, an insert with a post in the +2 anterior position will result in approximately 2 mm less rollback than an insert having a post in the neutral position. An insert with a post in the +4 anterior position will result in approximately 4 mm less rollback than an insert having a post in the neutral position. An appropriate permanent insert is selected based on the fit of the trial inserts.

Figure 14:
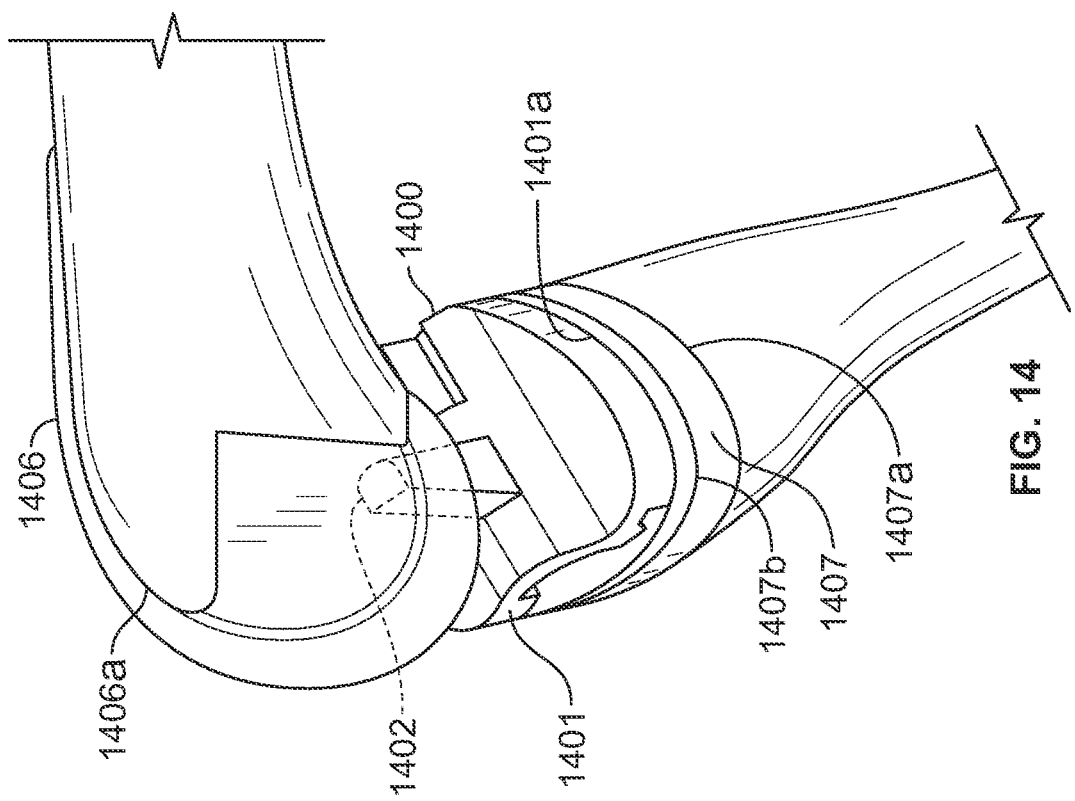
FIG. 14 is a side view of a replacement joint. The replacement joint comprises a permanent tibial insert with an immovable posterior stabilizing post in the neutral position.
Figure 13:
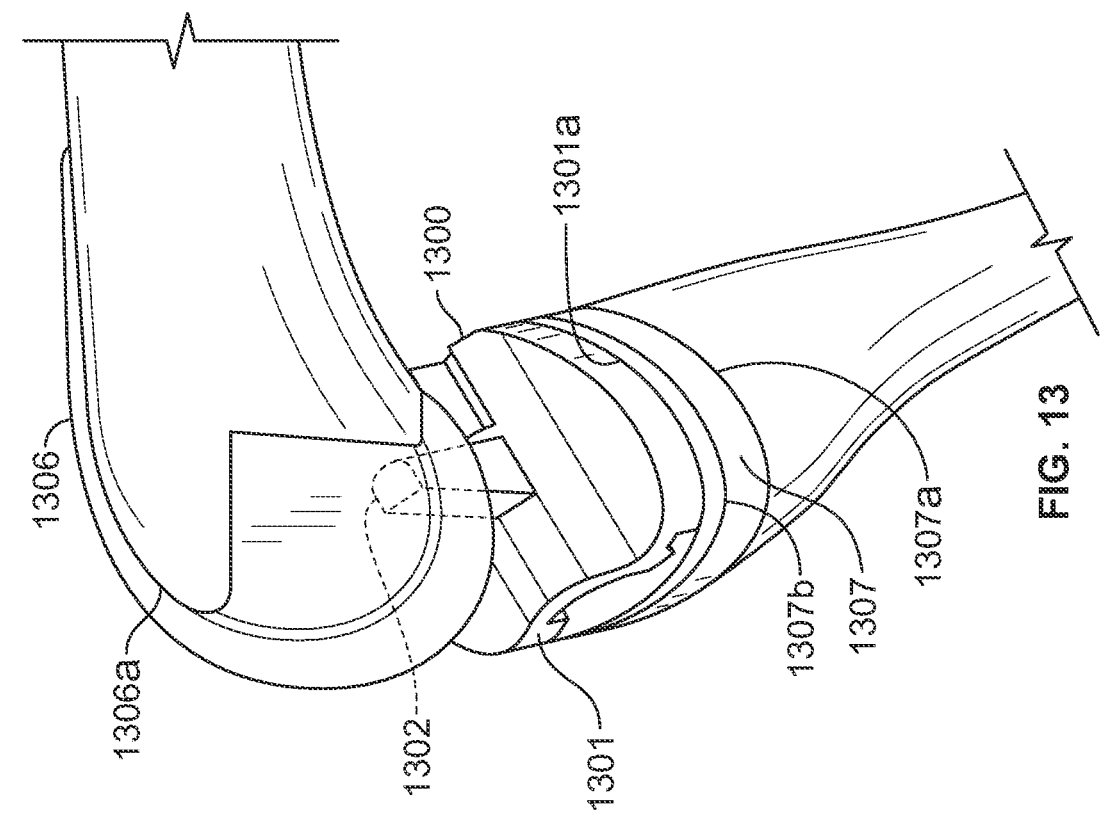
FIG. 13 is a side view of a replacement joint. The replacement joint comprises a permanent tibial insert with an immovable posterior stabilizing post in the +4 anterior position.

In certain embodiments, the inserts disclosed herein can be selected or configured to provide the amount of rollback desired by a user. Certain permanent inserts described herein can be configured with the post in a pre-selected position. The pre-selected position determines the rollback of the joint. FIGS. 13 and 14 depict how the position of the posterior stabilizing post controls the maximum rollback of the replacement joint.

FIG. 13 shows a permanent tibial insert 1300 with an immovable posterior stabilizing post 1302 in the anterior +4 position relative to the base 1301, and FIG. 14 shows a permanent tibial insert 1400 with an immovable posterior stabilizing post 1402 in the neutral position relative to the base 1401. In FIG. 13, the joint's maximum rollback is 4 mm less than in FIG. 14 because in FIG. 13 the posterior stabilizing post is in the +4 anterior position. The +4 position allows less rollback than the neutral position, preventing over-stretching of soft tissues. In FIG. 14, the joint can undergo full rollback because the posterior stabilizing post is in the neutral position.

In FIG. 13, a permanent tibial insert 1300 couples a femoral component 1306 to a tibial component 1307. In FIG. 14, just as in FIG. 13, a permanent tibial insert 1400 couples a femoral component 1406 to a tibial component 1407. In both Figures, the femoral component is immovably coupled to the patient's femur, and the tibial component is immovably coupled to the patient's tibia. Various methods may be suitable for coupling femoral and tibial components to the bone. In some embodiments, the femoral component or tibial component has a protruding fixture that extends into the bone. In some embodiments, the bone-facing side of the tibial component 1307a or 1407a and/or the bone-facing side of the femoral component 1306a or 1406a comprises a roughened surface or porous material to encourage bone in-growth. As the bone grows into the roughened or porous surface, the bone becomes more tightly linked to the implant, strengthening the joint. The permanent tibial insert attaches immovably to the tibial component, with the lower surface 1301a or 1401a of the insert aligning with and fixed relative to the upper surface 1307a or 1407a of the tibial component. In contrast, the permanent tibial insert can move like a hinge relative to the femoral component, and this hinge-like motion allows the knee to flex. In FIG. 13 the post 1302 is more anterior, so there is less rollback; in FIG. 14 the post 1402 is more posterior, so there is more rollback.

In certain implementations, a user can use the set of trial inserts in FIG. 12 to select a permanent insert, such as that of FIG. 13 or 14, of the correct size and shape. To do so, the user (e.g., a surgeon or surgeon's assistant) sequentially evaluates at least two trial inserts in a patient during the course of total knee replacement surgery. This surgery comprises, briefly, implanting a femoral component, implanting a tibial component, and adding an insert between them. Specifically, the distal end of the femur is resected and the proximal end of the tibia is resected. These cuts may be made with a bone saw, using a cutting block for guidance. The ACL and PCL can be excised from the tibia and femur so they do not interfere with the replacement joint. Next, the gap between the resected tibia and femur is assessed when the knee is extended, using a spacer. If the gap is insufficient for the replacement joint, the bones can be further resected. A femoral component of an appropriate size is chosen, for instance by testing different trial femoral components. The gap between the tibia and femur is assessed when the knee is flexed. If the gap is too small, the tibia can be further resected or a different size of femoral component can be chosen. The permanent femoral component is placed against the femur and affixed with bone spikes. After the femoral component is in place, the tibial component can be implanted. The tibial component generally has a stem extending into the medullary cavity of the tibia, creating a stable attachment to the tibia, and a tibial component lying at the proximal end of the tibia. A bone spike can be used to affix the tibial component to the tibia. Next, the appropriate insert is chosen.

The user can also evaluate two, three, or four, or more inserts sequentially. Each trial insert has a posterior stabilizing post immovably coupled to a base. The user connects each trial insert to the tibial component and the femoral component in the patient's joint. The trial inserts may be, for example, those shown in FIG. 12. The user then bends the patient's knee with each insert in place. The user then evaluates the fit of the trial insert relative to fitting criteria. Fitting criteria balance different factors to identify a suitable fit for a patient. The fitting criteria may take into account whether the patient's knee has sufficient rollback to allow the patient a sufficient range of motion. The fitting criteria may also take into account whether the soft tissues anterior to the knee are unduly stretched when the knee experiences the maximum rollback permitted by the insert. Based on the evaluation of the fit, the user determines a desired location of the post. This allows the user to select a permanent tibial insert comprising a base coupled to a posterior stabilizing post at a position corresponding to the determined location. In some embodiments, the permanent tibial insert has a posterior stabilizing post that is immovably coupled to the base. In other embodiments, the permanent tibial insert is an insert like that of FIG. 2, where the user can move the post to the desired position before or during surgery, and the post will remain in the desired position after surgery due to a locking insert.

A user can also determine the correct size and shape for a permanent tibial insert using a trial insert with a moveable posterior stabilizing post. Examples of such trial inserts are shown in FIG. 1 (where the post locks in place) and FIG. 8 (where the post does not lock). The user places the tibial insert in the patient. The user connects the trial insert to a tibial component and a femoral component in the patient's joint. The user then evaluates at least two fits of the trial insert relative to fitting criteria with the post at two or more respective positions relative to the base. In some embodiments, the user removes the trial insert every time he or she repositions the post, and in other embodiments, the user repositions the post while the insert is disposed in the patient's joint. Based on the evaluations of the fit, the user can determine a desired location of the post. This allows the user to select a permanent tibial insert comprising a base coupled to a posterior stabilizing post at a position corresponding to the determined location. In some embodiments, the permanent tibial insert has a posterior stabilizing post that is immovably coupled to the base. In other embodiments, the permanent tibial insert is an insert like that of FIG. 2, where the user can move the post to the desired position before or during surgery, and the post will remain in the desired position after surgery due to a locking insert.

In addition to testing different positions for the post, the user can also test other variations in size and shape of insert. For example, a user can also test inserts in which the base has different thicknesses. A proper thickness of base allows the insert to fill the space between the tibial component and femoral component without unduly pressing the femur and tibia apart. The user can also test inserts in which the base has different radii in the anterior/posterior or lateral/medial directions.

Once the appropriate permanent insert is selected, the insert is coupled to the tibial component. In some embodiments, a locking mechanism immovably couples the tibial component to the insert. The insert is then coupled to the femoral component, in some instances by inserting the posterior stabilizing post into a hole situated between the condyles of the femoral component. Cement is applied to the tibial component and femoral component to affix them permanently to the tibia and femur, respectively.

In some embodiments, an insert (e.g., a trial insert) is part of a kit or instrument tray comprising other tools that can be used in total knee arthroplasty. The kit may also comprise cutting blocks, saw blades, bone cement, and bone spikes.

It is to be understood that the foregoing description is merely illustrative and is not to be limited to the details given herein. While several embodiments have been provided in the present disclosure, it should be understood that the disclosed systems, devices, and methods, and their components, may be embodied in many other specific forms without departing from the scope of the disclosure.

Variations and modifications will occur to those of skill in the art after reviewing this disclosure. The disclosed features may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. An orthopedic insert comprising:
    a base having an anterior end and a posterior end,
    a posterior stabilizing post coupled to the base, the posterior stabilizing post including an anterior face that outwardly extends to a position beyond the base, the posterior stabilizing post being adjustably positionable relative to the base along a trough of the base, the trough not extending through the anterior and posterior ends of the base, wherein the posterior stabilizing post is positionable between an anterior block wall and a posterior block wall of the base, and
    first and second locking inserts that extend through the anterior and posterior block walls, respectively, the first locking insert contacting the anterior face of the posterior stabilizing post, the second locking insert contacting a posterior face of the posterior stabilizing post to lock the posterior stabilizing post in place relative to the base; and
    wherein the posterior stabilizing post slides within the trough.

2. The insert of claim 1, wherein the locking insert is selected from a ball and detent, screws, or tabs.

3. The insert of claim 1, which is a non load-bearing trial insert.

4. The insert of claim 1, wherein the insert is a tibial insert.

5. A knee implant comprising the tibial insert of claim 4, further comprising a femoral component structured to engage the posterior stabilizing post and to slide the posterior stabilizing post relative to the base during flexion.

6. A knee implant comprising:
    a tibial component shaped to align with and support the proximal end of a patient's tibia;
    a femoral component shaped to align with and support the patient's femur; and
    a tibial insert comprising a base and a posterior stabilizing post coupled to the base, the base having an anterior end and a posterior end, a portion of the posterior stabilizing post extending away from the base and structured to engage the femoral component, the posterior stabilizing post being adjustably positionable relative to the base, and wherein the posterior stabilizing post is biased by a resilient member in a direction toward one of the anterior end and the posterior end of the base, the resilient member being disposed in a trough in the base, the resilient member extending from an end of the trough to the posterior stabilizing post such that a first end of the resilient member contacts the end of the trough and a second end of the resilient member opposite the first end contact the posterior stabilizing post,
    a first locking insert that extends through the anterior end of the base; and
    a second locking insert that extends through the posterior end of the base;
    wherein the first and second locking inserts lock the posterior stabilizing post in place relative to the base.

7. The knee implant of claim 6, wherein the resilient member modulates anterior-posterior movement of the posterior stabilizing post relative to the base based on a force applied to the posterior stabilizing post by the femoral component.

8. The knee implant of claim 7, wherein the femoral component comprises a cam; and
    wherein the resilient member modulates anterior-posterior movement of the posterior stabilizing post relative to the base based on a force applied to the posterior stabilizing post by the cam.

9. The knee implant of claim 8, wherein the cam comprises a rod extending between femoral condyles of the femoral component.

10. The knee implant of claim 6, wherein the femoral component is configured to slide the posterior stabilizing post along the base as the femoral component engages the posterior stabilizing post such that the posterior stabilizing post compresses and expands the resilient member during flexion and extension.

11. A tibial insert comprising:
    a base;

a posterior stabilizing post coupled to the base and configured to slide relative to the base, the posterior stabilizing post adapted to couple to a femoral component; and a resistance member disposed within the base, wherein the resistance member compresses when the posterior stabilizing post slides anteriorly with respect to the base from a force applied to the posterior stabilizing post by the femoral component during movement of a corresponding knee joint from extension to flexion, wherein the resistance member is disposed in a trough in the base, the trough having anterior and posterior interior ends, wherein a first end of the resistance member contacts an interior end of the trough and a second end of the resistance member contacts the post, and first and second locking inserts that extend through the anterior and posterior interior ends of the trough, respectively, to lock the posterior stabilizing post in place relative to the base.

12. The insert of claim 11, wherein the resistance member is affixed to the base.

13. The insert of claim 11, wherein the insert is configured to attach immovably to a tibial component.

14. The insert of claim 11, wherein the first end of the resistance member contacts the anterior interior end of the trough.

15. The insert of claim 11, wherein the resistance member is a spring.

16. The tibial insert of claim 11, wherein the resistance member applies a resistance member force to the posterior stabilizing post; and wherein a cam of the femoral component applies a cam force to the posterior stabilizing post during contact with the posterior stabilizing post.

17. The tibial insert of claim 16, wherein the resistance member force is at least as great as the cam force with the corresponding knee joint is in extension; and wherein the cam force exceeds the resistance member force as the corresponding knee joint is flexed causing the posterior stabilizing post to move anteriorly relative to the base.

18. A tibial insert comprising:

a base having a trough defined in a superior face of the base and extending in an anterior-posterior direction between an anterior trough wall and a posterior tough wall;

a spring-actuated posterior stabilizing post coupled to the base and configured to slide relative to the base, wherein the posterior stabilizing post includes an anterior face and a posterior face positioned within the trough; and a spring coupled to one of the anterior trough wall and the posterior trough wall at a first end and to one of the anterior face and the posterior face at a second end, the spring adapted to compress or extend when the posterior stabilizing post slides with respect to the base, and first and second locking screws that extend through the anterior trough wall and posterior trough wall of the base, respectively, the first locking screw contacting the anterior face of the posterior stabilizing post, the second locking insert contacting the posterior face of the posterior stabilizing post to lock the posterior stabilizing post in place relative to the base.

19. The insert of claim 18, wherein the trough has a superior portion of a first width and an inferior portion of a second width greater than the first width, each of the superior portion and the inferior portion extending an entirety of the trough in the anterior-posterior direction.

20. The tibial insert of claim 18, wherein the spring-actuated posterior stabilizing post is configured to slide anterior-posteriorly relative to the base in response to a force applied to the spring-actuated posterior stabilizing post by a femoral component.

* * * * *